United States Patent [19]

Narisada et al.

[11] 4,138,486

[45] Feb. 6, 1979

[54] ARYLMALONAMIDO-1-OXADETHIACEPH-ALOSPORINS

[75] Inventors: Masayuki Narisada, Ibaraki; Wataru Nagata, Nishinomiya, both of Japan

[73] Assignee: Shionogi & Co., Ltd., Osaka, Japan

[21] Appl. No.: 780,183

[22] Filed: Mar. 22, 1977

[30] Foreign Application Priority Data

Mar. 25, 1976 [JP] Japan .................................. 51-33401
Apr. 30, 1976 [JP] Japan .................................. 51-50295

[51] Int. Cl.² .................. A61K 27/00; A61K 31/695; A61K 31/555
[52] U.S. Cl. .............................. 424/248.52; 424/184; 424/245; 544/90
[58] Field of Search ............... 260/244 R; 424/248.51, 424/248.52, 184, 245; 544/90

[56] References Cited

U.S. PATENT DOCUMENTS

| | | | |
|---|---|---|---|
| 3,728,342 | 4/1973 | Kukolja ........................... | 260/243 C |
| 3,769,277 | 10/1973 | Long et al. ....................... | 260/243 C |
| 3,795,672 | 3/1974 | Murphy ............................ | 260/243 C |
| 4,011,216 | 3/1977 | Menard et al. .................... | 260/244 R |
| 4,013,648 | 3/1977 | Horning et al. ................... | 260/244 R |
| 4,013,653 | 3/1977 | Wolfe .............................. | 260/244 R |

FOREIGN PATENT DOCUMENTS 832174 1/1975 Belgium.
1914366 10/1970 Fed. Rep. of Germany.
2355209 3/1974 Fed. Rep. of Germany.
2355210 3/1974 Fed. Rep. of Germany.

OTHER PUBLICATIONS

J. Heterocyclic Chem. 5, 779–783 (1968) - Sheehan et al., "The Synthesis of Oxygen Analogs of Cepham".

*Primary Examiner*—Albert T. Meyers
*Assistant Examiner*—D. W. Robinson
*Attorney, Agent, or Firm*—Wenderoth, Lind & Ponack

[57] ABSTRACT

Antibacterial 1-oxadethiacephalosporins of the formula:

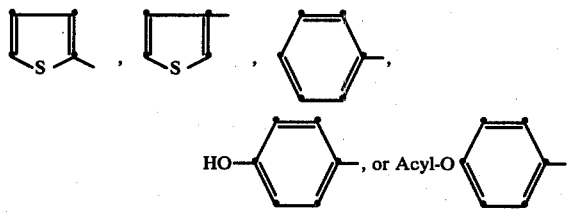

[wherein Ar is

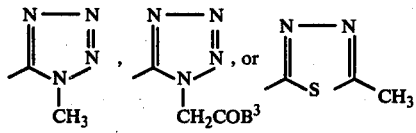

(in which Acyl is organic or inorganic acyl);
$COB^1$ and $COB^2$ each is carboxy or protected carboxy;
Het is

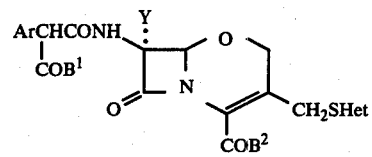

(in which $COB^3$ is carboxy or protected carboxy);
and Y is hydrogen or methoxy;

and when $COB^1$, $COB_2$, and/or $COB^3$ is carboxy, pharmaceutically acceptable salts thereof are included, but with a proviso that when Y is methoxy, Het is

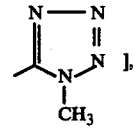

], a pharmaceutical or veterinary composition comprising the said 1-oxadethiacephalosporins and pharmaceutical carrier, and a method for treating or preventing human or veterinary infectious diseases comprising administering the said 1-oxadethiacephalosporin.

41 Claims, No Drawings

ARYLMALONAMIDO-1-OXADETHIACEPHALOSPORINS

This invention relates to arylmalonamido-1-oxadethiacephalosporins. More specifically, it relates to compounds of the following formula:

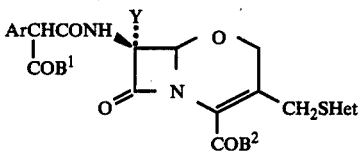

[wherein Ar is

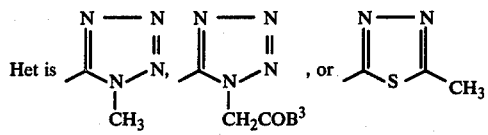

(in which Acyl is organic or inorganic acyl);
COB¹ and COB² each is carboxy or protected carboxy; Het is

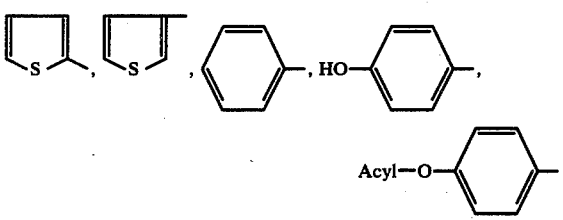

(in which COB³ is carboxy or protected carboxy); and
Y is hydrogen or methoxy;
and when COB¹, COB², and/or COB³ is carboxy, pharmaceutically acceptable salts thereof;
with a proviso that when Y is methoxy, Het is

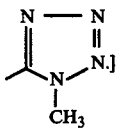

Cephalosporin analogs having oxygen in place of sulfur atom in the nucleus have been described in the Journal of Heterocyclic Chemistry, Volume 5, page 779 (1968) by J. C. Sheehan and M. Dadic; German Patent Application (OLS) No. 2,219,601 (1972); the Canadian Journal of Chemistry, Volume 52, page 3996 (1974 by S. Wolfe et al.; the Journal of American Chemical Society, Volume 96, page 7582 (1974) by B. G. Christensen et al.; and Japanese Patent Application (OPI No. 49-133594) claiming priorities based on U.S. Pat. application Nos. 303,905 and 395,662.

The present inventors have now prepared various 1-oxadethiacephalosporins closely related to known (1-thia)cephalosporins. Contrary to the reports of B. G. Christensen et al., suggesting their racemic 1-oxadephalosporins showed about a half the potency of (1-thia)cephalosporins, the optically active products prepared by the present inventors were more active as the corresponding (1-thia)cephalosporins in their antibacterial property. However, the β-lactam ring of the prior art 1-oxadethiacephalosporins was less stable to be clinical drugs, than that of (1-thia)cephalosporins.

Compounds (I) selected from the optically active compounds prepared by the present inventors overcome the said deficiency of 1-oxadethiacephalosporins.

Furthermore, Compounds (I) showed the following characteristics when compared with other types of 1-oxadethiacephalosporins:

(1) more potent antibacterial activity against gram negative b bacteria;
(2) higher stability of the β-lactam ring;
(3) closer minimal inhibitory concentration between the bacteria producing and non-producing β-lactamase;
(4) less dependency on inoculum size;
(5) higher effectiveness against bacteria resistant to certain other cephalosporins (e.g. Enterobacteria, Serratia, indole positive Proteus);
(6) higher contribution of bactericidal character; and
(7) higher blood level.

Additionally, Compounds (I) where Y is methoxy have the following superiorities:
(a) broader antibacterial spectra (e.g. 3.6 μg/ml or more against Pseudomonas sp.), and anaerobic bacteria (*Bacteroid fragilis*);
(b) higher potency against bacteria producing β-lactamase;
(c) higher stability in blood; and
(d) lower binding with serum proteins.

In the formula (I), preferably Ar is 3-thienyl, p-hydroxyphenyl, and p-acyloxyphenyl in which the acyl is 1-5C alkanoyl, carbamoyl, 2-6C N-alkylcarbamoyl, or ureidocarbonyl.

The group Acyl in the definition of Ar can be inorganic or organic acyls containing up to 20 carbon atoms especially 1-5C alkanoyl, 2-5C alkoxycarbonyl, 8-20C aralkoxycarbonyl, carbamoyl, 2-6C N-alkylcarbamoyl, and ureidocarbonyl.

Specific examples of the acyls include formyl, acetyl, propionyl, butyryl, isobutyryl, carbethoxycarbonyl, benzyloxycarbonyl, carbamoyl, N-methylcarbamoyl, N-ethylcarbamoyl, N-propylcarbamoyl, N-isobutylcarbamoyl, N,N-dimethylcarbamoyl, carbamoylcarbamoyl, $N^\alpha$-methylureidocarbonyl, and like acyls.

The group COB¹, COB², and COB³ can be carboxy or protected carboxy conventional in the chemistry of penicillins and cephalosporins, usually containing up to 20 carbon atoms. The protective groups can be the same or different for each carboxy in the molecule. Usually, the protective groups are removed to give free carboxy or salts, at any stage of synthesis of Compounds (I). Therefore, the structures of the carboxyprotective groups can vary widely without changing the gist of this invention. In other words, their structures have no specific significance other than protection, deprotection, and when included, salt formation.

Specific examples of said protective groups are esters (including optionally substituted 1-5C alkyl esters e.g. methyl, ethyl, isopropyl, n-butyl, t-butyl, pentyl, cyclopropylmethyl, monohydroxy-t-butyl, 2,2,2-trichloroethyl, chloromethyl, cyanomethyl, methanesulfonylethyl, acetylmethyl, acetoxymethyl, propionyloxymethyl, benzoyloxymethyl, methoxymethyl, phenoxymethyl, methylthiomethyl, phenylthiomethyl, tetrahydropyranyl, phthalimidomethyl, α,α-dimethylpropargyl, ethoxycarbonyloxyethyl, methoxycarbonyloxypropyl, and allyl esters; aralkyl esters e.g. benzyl, phenethyl, tolylmethyl, dimethylbenzyl, nitrobenzyl, halobenzyl, methoxybenzyl, phthalidyl, p-hydroxy-di-t-butylbenzyl, diphenylmethyl, trityl, phenacyl, chlorophenacyl, bromophenacyl, nitrophenacyl, and methylphenacyl esters; and another easily removable aliphatic esters; metal esters e.g. trimethylsilyl, dimethylmethoxysilyl, trimethylstannyl esters; and aromatic esters e.g. phenyl, naphthyl, tolyl, dimethylphenyl, nitrophenyl, methanesulfonylphenyl, chlorophenyl, pentachlorophenyl, indanyl, and pyridyl esters); or pharmaceutically acceptable salts (including alkali metal salts e.g. sodium and potassium salts; alkaline earth metal salts e.g. magnesium, calcium, and acyloxycalcium salts; and salts with organic bases e.g. procain, triethylamine, and dicyclohexylamine). Each carboxy in the molecule can be free or protected by the same or different groups.

Preferably $COB^1$, $COB^2$, and/or $COB^3$ can be free carboxy or its pharmaceutically acceptable salts (e.g. sodium and potassium salts).

Some carboxy protective groups are, however, useful for changing the character of the products as drugs. In such cases, they can be specifically known groups for drugs conventional in the art. These groups include those forming the following pharmaceutically acceptable esters for enhancing the absorption through digestive organs: e.g. phthalidyl, acetoxymethyl, pivaloyloxymethyl, acetoxyethyl, propionyloxyethyl, indanyl, phenyl, tolyl, dimethylphenyl, methoxyphenyl, methoxycarbonyloxyethyl, ethoxycarbonylmethyl, phenacyl, and like esters.

Preferably Y is methoxy, although Y being hydrogen is also important.

Usually, Compounds (I) are administered as salts for the parenteral administration to human or veterinary subjects. Most preferable salts are sodium or potassium salts, or salts with pharmaceutically acceptable organic bases e.g. procain or xylocain. The salt functions are selected from the view point of safety, solubility, stability, etc.

Specific examples of Compounds (I) include the following ones:

7β-[α-(2-thienyl)-α-carboxyacetamido]-3-(1-methyltetrazol-5-yl)thiomethyl-1-oxadethia-3-cephem-4-carboxylic acid, 7β-[α-(2-thienyl)-α-carboxyacetamido]-3-(1-carboxymethyltetrazol-5-yl)thiomethyl-1-oxadethia-3-cephem-4-carboxylic acid, 7β-[α-(2-thienyl)-α-carboxyactamido]-3-(2-methyl-1,3,4-thiadiazol-5-yl)thiomethyl-1-oxadethia-3-cephem-4-carboxylic acid, 7β-[α-(3-thienyl)-α-carboxyacetamido]-3-(1-methyltetrazol-5-yl)thiomethyl-1-oxadethia-3-cephem-4-carboxylic acid, 7β-[α-(3-thienyl)-α-carboxyacetamido]-3-(1-carboxymethyltetrazol-5-yl)thiomethyl-1-oxadethia-3-cephem-4-carboxylic acid, 7β-[α-(3-thienyl)-α-carboxyacetamido]-3-(2-methyl-1,3,4-thiadiazol-5-yl)thiomethyl-1-oxadethia-3-cephem-4-carboxylic acid, 7β-(α-phenyl-α-carboxyacetamido)-3-(1-methyltetrazol-5-yl)thiomethyl-1-oxadethia-3-cephem-4-carboxylic acid, 7β-(α-phenyl-α-carboxyacetamido)-3-(1-carboxymethyltetrazol-5-yl)thiomethyl-1-oxadethia-3-cephem-4-carboxylic acid, 7β-(α-phenyl-α-carboxyacetamido)-3-(2-methyl-1,3,4-thiadiazol-5-yl)thiomethyl-1-oxadethia-3-cephem-4-carboxylic acid, 7β-(α-p-hydroxyphenyl-α-carboxyacetamido)-3-(1-methyltetrazol-5-yl)thiomethyl-1-oxadethia-3-cephem-4-carboxylic acid, 7β-(α-p-hydroxyphenyl-α-carboxyacetamido)-3-(1-carboxymethyltetrazol-5-yl)thiomethyl-1-oxadethia-3-cephem-4-carboxylic acid, 7β-(α-p-hydroxyphenyl-α-carboxyacetamido)-3-(2-methyl-1,3,4-thiadiazol-5-yl)thiomethyl-1-oxadethia-3-cephem-4-carboxylic acid, 7β-(α-p-acetoxyphenyl-α-carboxyacetamido)-3-(1-methyltetrazol-5-yl)thiomethyl-1-oxadethia-3-cephem-4-carboxylic acid, 7β-(α-p-acetoxyphenyl-α-carboxyacetamido)-3-(1-carboxymethyltetrazol-5-yl)thiomethyl-1-oxadethia-3-cephem-4-carboxylic acid, 7β-(α-p-acetoxyphenyl-α-carboxyacetamido)-3-(2-methyl-1,3,4-thiadiazol-5-yl)thiomethyl-1-oxadethia-3-cephem-4-carboxylic acid, 7β-(α-p-propionyloxyphenyl-α-carboxyacetamido)-3-(1-methyltetrazol-5-yl)thiomethyl-1-oxadethia-3-cephem-4-carboxylic acid, 7β-(α-p-pentanoyloxyphenyl-α-carboxyacetamido)-3-(2-methyl-1,3,4-thiadiazol-5-yl)thiomethyl-1-oxadethia-3-cephem-4-carboxylic acid, 7β-(α-carbamoyloxyphenyl-α-carboxyacetamido)-3-(1-methyltetrazol-5-yl)thiomethyl-1-oxadethia-3-cephem-4-carboxylic acid, 7β-(α-p-N-methylcarbamoyloxyphenyl-α-carboxyacetamido)-3-(1-methyltetrazol-5-yl)thiomethyl-1-oxadethia-3-cephem-4-carboxylic acid, 7β-(α-p-N-pentylcarbamoyloxyphenyl-α-carboxyacetamido)-3-(2-methyl-1,3,4-thiadiazol-5-yl)thiomethyl-1-oxadethia-3-cephem-4-carboxylic acid, 7β-(α-p-ureidocarbonyloxyphenyl-α-carboxyacetamido)-3-(1-methyltetrazol-5-yl)thiomethyl-1-oxadethia-3-cephem-4-carboxylic acid, 7β-[α-(2-thienyl)-α-carboxyacetamido]-7α-methoxy-3-(1-methyltetrazol-5-yl)thiomethyl-1-oxadethia-3-cephem-4-carboxylic acid, 7β-[α-(3-thienyl)-α-carboxyacetamido]-7α-methoxy-3-(1-methyltetrazol-5-yl)thiomethyl-1-oxadethia-3-cephem-4-carboxylic acid, 7β-(α-phenyl-α-carboxyacetamido)-7α-methoxy-3-(1-methyltetrazol-5-yl)thiomethyl-1-oxadethia-3-cephem-4-carboxylic acid, 7β-(α-p-hydroxyphenyl-α-carboxyacetamido)-7α-methoxy-3-(1-methyltetrazol-5-yl)thiomethyl-1-oxadethia-3-cephem-4-carboxylic acid, 7β-(α-p-acetoxyphenyl-α-carboxyacetamido)-7α-methoxy-3-(1-methyltetrazol-5-yl)thiomethyl-1-oxadethia-3-cephem-4-carboxylic acid, 7β-(α-p-propionyloxyphenyl-α-carboxyacetamido)-7α-methoxy-3-(1-methyltetrazol-5-yl)thiomethyl-1-oxadethia-3-cephem-4-carboxylic acid, 7β-(α-p-benzoyloxyphenyl-α-carboxyacetamido)-7α-methoxy-3-(1-methyltetrazol-5-yl)thiomethyl-1-oxadethia-3-cephem-4-carboxylic acid, 7β-(α-p-carbamoyloxyphenyl-α-carboxyacetamido)-7α-methoxy-3-(1-methyltetrazol-5-yl)thiomethyl-1-oxadethia-3-cephem-4-carboxylic acid, 7β-(α-p-N-methylcarbamoyloxyphenyl-α-carboxyacetamido)-7α-methoxy-3-(1-methyltetrazol-5-yl)thiomethyl-1-oxadethia-3-cephem-4-carboxylic acid, 7β-(α-p-N-propylcarbamoyloxyphenyl-α-carbox-yacetamido)-7α-methoxy-3-(1-methyltetrazol-5-yl)thiomethyl-1-oxadethia-3-cephem-4-carboxylic acid, 7β-(α-p-ureidocarbonyloxyphenyl-α-carbox-yacetamido)-7α-methoxy-3-(1-methyltetrazol-5-yl)thiomethyl-1-oxadethia-3-cephem-4-carboxylic acid, 7β-(α-p-N$^α$-methylureidocarbonyloxyphenyl-α-carboxyacetamido)-7α-methoxy-3-(1-methyltetrazol-5-yl)thiomethyl-1-oxadethia-3-cephem-4-carboxylic acid, 7β-[α-phenyl-α-(5-indanyloxy)carbonylacetamido]-3-(1-methyltetrazol-5-yl)thiomethyl-1-oxadethia-3-cephem-4-carboxylic acid, 7β-[α-phenyl-α-(5-indanyloxy)carbonylacetamido]-7α-methoxy-3-(1-methyltetrazol-5-yl)thiomethyl-1-oxadethia-3-cephem-4-carboxylic acid, 7β-[α-(3-thienyl)-α-(5-indanyloxy)carbonylacetamido]-7α-methoxy-3-(1-methyltetrazol-5-yl)thiomethyl-1-oxadethia-3-cephem-4-carboxylic acid, 7β-[α-(3-thienyl)-α-phenoxycarbonylacetamido]-7α-methoxy-3-(1-methyltetrazol-5-yl)thiomethyl-1-oxadethia-3-cephem-4-carboxylic acid, 7β-[α-(3-thienyl)-α-(3,4-dimethylphenoxy)carbonylacetamido]-7α-methoxy-3-(1-methyltetrazol-5-yl)thiomethyl-1-oxadethia-3-cephem-4-carboxylic acid, 7β-[α-p-hydroxyphenyl-α-(5-indanyloxy)carbonylacetamido]-7α-methoxy-3-(1-methyltetrazol-5-yl)thiomethyl-1-oxadethia-3-cephem-4-carboxylic acid, Pivaloyloxymethyl 7β-[α-p-hydroxyphenyl-α-carboxyacetamido)-7α-methoxy-3-(1-methyltetrazol-5-yl)thiomethyl-1-oxadethia-3-cephem-4-carboxylate, and their pharmaceutically acceptable salts (especially sodium and potassium salts). As intermediates for these free acids and salts, esters of the said compounds with ester groupings are also important. These include t-butyl, t-amyl, 2,2,2-trichloroethyl, acyloxymethyl, diphenylmethyl, trityl, benzyl, nitrobenzyl, methoxybenzyl, phenacyl, phenyl, indanyl, trimethylsilyl, trimethylstannyl, methoxydimethylsilyl esters, and like esters.

Compounds (I) having 1-methyltetrazol-5-ylthiomethyl at position 3 are strongest antibacterial drugs against gram negative bacteria accompanied with less drop of the activity at higher inoculum size.

Compounds (I) having 1-carboxymethyltetrazol-5-ylthiomethyl at position 3 show stronger antiinfection effect in vivo than expected from in vitro data, because of their capability of achieving a high blood level.

Compounds (I) having phenylmalonamido, (2-thienyl)malonamido, or (3-thienyl)malonamido at position 7 show potent antibacterial activity particularly against gram negative bacteria.

Compounds (I) having p-hydroxyphenyl-malonamido, p-acetoxyphenylmalonamido, p-carbamoyloxyphenylmalonamido, p-N-methylcarbamoyloxyphenylmalonamido, or p-ureidocarbonyloxyphenylmalonamido at position 7 are potent antibacterials less deactivated in living animals because of their lower protein binding and of their higher blood level than those of the corresponding unsubstituted aryl-malonamido compounds. They also show highly intensified activity against some Pseudomonas strains including those resistant to carbenicillin.

Compounds (I) having methoxy for Y at position 7α are more stable against β-lactamase, more broadly effective (e.g. improved activity against Pseudomonas bacteria and other gram negative bacteria), and more potent than those having hydrogen for Y.

All Compounds (I) are novel substances showing potent antibacterial activity and useful medicines, veterinary drugs, and disinfectants. For example, they are conventionally given orally or parenterally to men or animals at a daily dose of e.g. 0.05 to 200 mg/kg body weight.

They are valuable antibiotics against various gram positive and negative bacteria, and useful as drugs for human and veterinary uses. They can be used for treating or preventing infections caused by gram positive bacteria (e.g. *Staphylococcus aureus, Streptococcus pyogenes, Bacillus subtilis, Bacillus cereus, Diplococcus pneumoniae, Corynebacterium diphtheriae*) and gram negative bacteria (e.g. *Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens*), and some are active even against *Pseudomonas aeruginosa* and anaerobic bacteria (e.g. *Bacteroid fragilis*). The compounds can be used also as disinfectants for preventing decay of perishables, additives to feedstuffs, or preventing bacterial growth of hygenical materials.

Further, Compounds (I) are also useful intermediates for preparing useful antibiotics within or beyond the scope of Compounds (I).

In order to show superior high activity of Compounds (I), minimal inhibitory concentrations of some Compounds (I) as sodium salts at an inoculum size of $10^8$ of gram negative bacteria on a nutrient agar plate of pH 7.0 are shown in Table I (Y=H), Table II (Y=OCH$_3$), in comparison to the other types of stereochemically pure 1-oxadethiacephalosporins in Table III.

The compounds (I) can be used in a wide variety of oral or parenteral dosage forms solely or in admixture with other coacting substances. The pharmaceutical compositions may be a mixture of 0.01 to 99% of Compound (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalent, suspensions, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose, syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate, emulsifying agents (e.g. lecithin, sorbitan monooleate, acacia); suspending agents (e.g. sorbitol, methyl cellulose, glucose, or sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g.

methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents to not exert adverse effect on the compounds, according to the methods conventional in the art.

As members of β-lactam antibiotics, Compounds (I) are not so stable enough to mix with various substances for a long time. Practically pure compounds and some inert additives are more preferable to make a drug for distribution (e.g. vials, capsules).

Compounds (I) having one or more carboxylic acid salt groups are soluble in water, and conveniently used as solution for intravenus, intramuscular, or subcutaneous injection according to a conventional method. The compounds can be dissolved in aqueous or oily solvents for injection to give a solution in an ampoule, but generally, more prolonged storage are possible by making a vial preparation containing crystals, powder, microcrystals, or lyophilizate of Compound (I), and dissolving or suspending the drug before use with the said solvents for injection. The preparation may contain preferably said preservative. The vial preparation or injection can be given to a patient at a daily dose of e.g. 0.05 to 50 mg/kg body weight depending on the infected bacteria, condition of the patient, and interval of the administration.

Compounds (I), especially those having $COB^1$ being a pharmaceutically acceptable ester groupsing (e.g. indanyl, acetoxymethyl, pivaloyloxymethyl, ethoxycarbonyloxyethyl, phenacyl, phthalidyl, phenyl, tolyl, xylyl, methoxyphenyl esters), can be absorbed through the digestive organ to some extent, and can be administered to human or veterinary subjects as powder, tablets, granules, capsules, dry syrup, emulsions, solution, suspension, and like oral preparations. They may be pure compounds or a composition comprising Compounds (I) and said pharmaceutical carriers. The preparation can be made according to the methods conventional in the art, and can be administered to a patient at a daily dose of e.g. 0.5 to 200 mg/kg body weight depending on the condition of patient and the diseases.

Further, Compounds (I) can be used as suppositories, ointments for topical or ocular use, powders for topical use, and like preparations preparable according to methods well known to those skilled in the art. The preparation can contain 0.01 to 99% of the Compound (I) together with a necessary amount of pharmaceutical carrier given above. A necessary amount e.g. 1 μg to 1 mg of the preparation can be applied to the affected part.

This invention also provides a method for treating or preventing human or veterinary bacterial infections by administering to the human or animal subject an effective amount of Compound (I) at a daily dose of e.g. 0.05 to 50 mg/kg body weight for injection or e.g. 0.5 to 200 mg/kg body weight for oral administration, or 1 μg to 1 mg for topical application, at an interval of e.g. 3 to 12 hours.

The method is applicable for treating or preventing some diseases caused by bacteria sensitive to Compounds (I) e.g. pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections, and pyelonephritis when caused by bacteria sensitive to Compound (I).

Preferably the Compounds (I) are given to a patient in forms of pharmaceutical preparations e.g. powder, dry syrup, tablets, troches, granules, capsules, pills, suppositories, injections, ointments, dispersions, inhalent, suspensions, solutions, emulsions, syrups, and elixirs. They may be in a unit dosage form e.g. tablets, troches, capsules, injections, vials, granules or powder in a separate container or package.

Preferble compounds (I) for the methods and preparations are those where Ar is 3-thienyl, p-hydroxyphenyl, or p-carbamoyloxyphenyl; $COB^1$ is carboxy or its pharmaceutically acceptable salt groups, 5-indanyloxycarbonyl, phenoxycarbonyl, dimethylphenoxycarbonyl, acetoxymethylcarbonyl, or pivaloyloxymethoxycarbonyl; $COB^2$ is carboxy or its pharmaceutically acceptable salt group; Het is 1-methyltetrazol-5-yl; and Y is hydrogen or methoxy.

Most preferable ones for the methods and preparations are following compounds:

7β-[α-(3-thienyl)-α-carboxyacetamido]-3-(1-methyltetrazol-5-yl)thiomethyl-1-oxadethia-3-cephem-4-carboxylic acid, its sodium salt, and its potassium salt;

7β-[α-(3-thienyl)-α-carboxyacetamido]-7α-methoxy-3-(1-methyltetrazol-5-yl)thiomethyl-1-oxadethia-3-cephem-4-carboxylic acid, its sodium salt and its potassium salt;

7β-(α-p-hydroxyphenyl-α-carboxyacetamido)-3-(1-methyltetrazol-5-yl)thiomethyl-1-oxadethia-3-cephem-4-carboxylic acid, its sodium salt, and its potassium salt;

7β-(α-p-hydroxyphenyl-α-carboxyacetamido)-7α-methoxy-3-(1-methyltetrazol-5-yl)thiomethyl-1-oxadethia-3-cephem-4-carboxylic acid, its sodium salt, and its potassium salt;

7β-(α-p-carbamoyloxyphenyl-α-carboxyacetamido)-3-(1-methyltetrazol-5-yl)thiomethyl-1-oxadethia-3-cephem-4-carboxylic acid, its sodium salt, and its potassium salt;

7β-(α-p-carbamoyloxyphenyl-α-carboxyacetamido)-7α-methoxy-3-(1-methyltetrazol-5-yl)thiomethyl-1-oxadethia-3-cephem-4-carboxylic acid, its sodium salt, and its potassium salt;

7β-[α-(3-thienyl)-α-(5-indanyloxy)carbonylacetamido]-7α-methoxy-3-(1-methyltetrazol-5-yl)thiomethyl-1-oxadethia-3-cephem-4-carboxylic acid and its sodium salt, 7β-[α-(3-thienyl)-α-phenoxycarbonylacetamido]-7α-methoxy-3-(1-methyltetrazol-5-yl)thiomethyl-1-oxadethia-3-cephem-4-carboxylic acid and its sodium salt, 7β-[α-(3-thienyl)-α-(3,4-dimethylphenoxy)carbonylacetamido]-7α-methoxy-3-(1-methyltetrazol-5-yl)thiomethyl-1-oxadethia-3-cephem-4-carboxylic acid and its sodium salt, and 7β-[α-p-hydroxyphenyl-α-(5-indanyloxy)carbonylacetamido]-7α-methoxy-3-(1-methyltetrazol-5yl)thiomethyl-1-oxadethia-3-cephem-4-carboxylic acid and its sodium salt.

Compounds (I) can, for example, be prepared by treating an Amine (II) with an Arylmalonic acid (III) or reactive derivatives thereof.

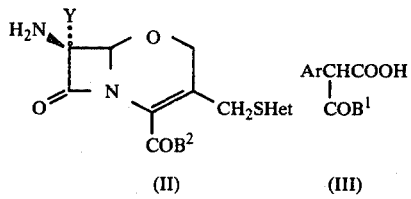

(wherein Ar, COB¹, COB², Het, and Y are as defined above)

The Compounds (II) are prepared in a manner analogus to the methods disclosed by German Patent Application (OLS) No. 2,355,209 (1974); Christensen et al., the Journal of American Chemical Society, Volume 96, page 7582; and U.S. Pat. No. 3,278,531 issued Oct. 11, 1966.

Compounds (III) or the derivatives thereof can be prepared in a manner analogous to the methods disclosed by Japanese Patent Application (OPI) No. 51-1489; German Patent Application (OLS) No. 2,451,931; and Journal of the American Chemical Society, Volume 59, page 1901 (1937) and Volume 91:8, page 2127, (1969).

When Arylmalonic acid (III) is used as free acid, the acylation is carried out in a solvent (particularly nitriles, ethers, amides, and halohydrocarbons for solvent or mixtures thereof) in the presence of a condensing reagent [e.g. N,N'-dialkylcarbodiimides (e.g. N,N'-diethylcarbodiimide, N,N'-dicyclohexylcarbodiimide); carbonyl compounds (e.g. carbonyldiimidazole); acylamines (e.g. 2-ethoxy-1-ethoxycarbonyl-1,2-dihydroquinoline); isoxazolinium salts (e.g. N-ethyl-5-phenylisoxazolinium-3-sulfonate, N-t-butyl-5-methylisoxazolinium perchlorate); and other condensing reagents] at about −10° C to about 70° C.

When Arylmalonic acid (III) is used in the forms of reactive derivatives for the acylation, it can be anhydrides [e.g. mixed anhydrides with alkylcarbonic acid, aralkylcarbonic acids, hydrohalogenic acids (acid halides), hydrogen azide (acid azide), phosphoric acid, phosphorous acid, sulfuric acid, sulfurous acid, hydrogen cyanide (acid cyanide); symmetrical intermolecular anhydrides; mixed anhydrides with aliphatic or aromatic sulfonic or carboxylic acids; special intramolecular anhydrides as ketene, isocyanate, and like reactive anhydrides]; reactive esters [e.g. enol ester; aryl ester (e.g. pentachlorophenyl, p-nitrophenyl, 2,4-dinitrophenyl, benzotriazole esters)]; diacylimino esters; reactive amides [e.g. amides with imidazole or triazole; reactive amides e.g. 2-ethoxy-1,2-dihydroquinolin-1-amide], and formimino derivatives (e.g. N,N-dialkyliminomethyl esters, N,N-diacylanilines).

If required, these acylating reagents can be used in the presence of an acid receptor [e.g. inorganic bases (e.g. hydroxides, carbonates, or bicarbonates of alkali metals or alkaline earth metals), organic bases (e.g. tertiary amines, aromatic bases), alkylene oxides (e.g. ethylene oxide, proypylene oxide), amides (e.g. N,N-dimethylformamide, hexamethylphosphorotriamide), and other acid receptors] or molecular sieves, preferably in a solvent (particularly ketone, ester, ether, nitrile, amide, halohydrocarbon solvents, or their mixtures).

The reaction is preferably carried out by contacting Amine (II) with Arylmalonic acid (III) or its reactive derivatives if required in the presence of a condensing reagent, acid receptor, dehydrating reagent, etc., preferably in a solvent at −50° C to +70° C for 10 minutes to 10 hours as is exemplified in the working examples.

The molar ratio of Amine (II) to Arylmalonic acid (III) or its derivative is about from 1 to 10, and more preferably from 1.0 to 2.0.

The mixture can be stirred, kept dry by exclusion of moisture with dehydrating materials (e.g. sodium hydroxide, soda lime), and can be kept under inert gas (e.g. nitrogen, argon).

The said solvents can be hydrocarbon (e.g. pentane, hexane, petroleum ether, benzene, toluene, xylene), halohydrocarbon (e.g. dichloromethane, chloroform, dichloroethane, chlorobenzene), ether (e.g. diethyl ether, methyl isobutyl ether, dioxane, tetrahydrofuran), ester (e.g. methyl acetate, ethyl acetate), ketone (e.g. acetone, methyl ethyl ketone, cyclohexanone), amide (e.g. dimethylformamide, hexamethylphosphorotriamide), sulfoxide (e.g. dimethylsulfoxide, diethylsulfoxide), nitrile (e.g. acetonitrile, benzonitrile), or nitroalkane (e.g. nitromethane, nitroethane, nitrobenzene), solvents or mixtures thereof. When so-called Schotten Bauman condition is applied for the acylation, alcohol (e.g. methanol, ethanol, isopropanol, t-butanol) or water can also be present in the reaction medium.

Alternatively, Compounds (I) can be prepared from the corresponding non-fused ring azetidinones by cyclization by e.g. Wittig reaction. For example, Azetidinone (IV) is heated in an inert solvent (e.g. ether, aromatic hydrocarbon, halohydrocarbon, amide, sulfoxide, and anhydride solvents) to give Compounds (I) in high yield.

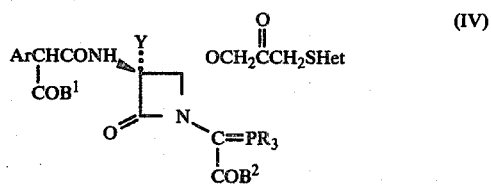

(wherein Ar, COB¹, COB², Het, and Y are defined above; and each of three R is equal or different, showing alkyl or aryl).

Compounds (IV) can, for example, be prepared from known substances by the method described below and in Preparations 3 through 5:

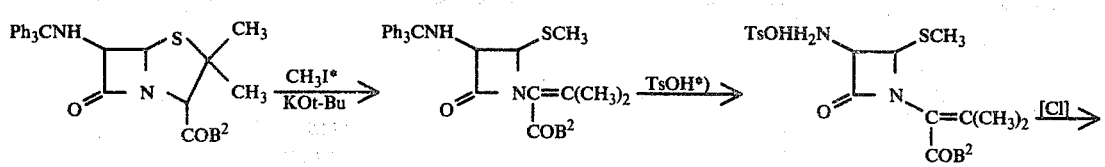

-continued

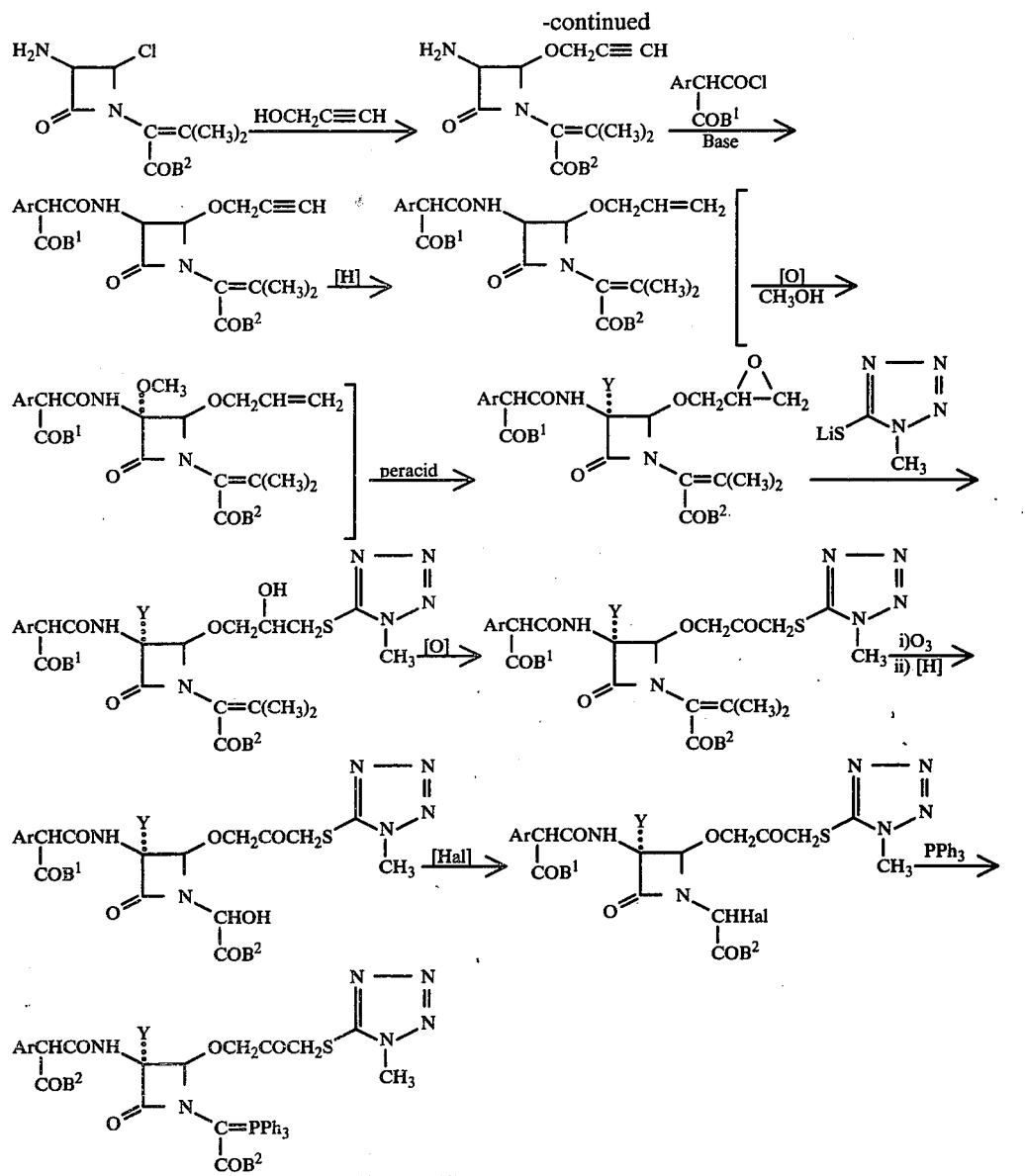

*Neyler et al.: Chem.Comm., 1971, 590; J.C.S. Perkin I, 1975, 562.

(wherein Ar, $COB^1$, $COB^2$, Het and Y are as defined above and Hal is halogen). The positions of acylation and introduction of methoxy can be changed so far as the substance is not suffered from the reaction.

When Ar is p-hydroxyphenyl, Compounds (I) can be treated with an inorganic or organic acylating reagent to give Compounds (I) where Ar is acyloxyphenyl. The acylating reagent and reaction condition are conventional in the art as is shown in Examples.

When Ar is p-hydroxyphenyl, Compounds (I) can at first be protected at its hydroxy with an easily removable protecting group and afterwards deprotected to give the desired hydroxyphenyl compounds. Representative protective groups can be those which form esters [including $C_1$–$C_6$ α-haloalkanoyl (e.g. trifluoroacetyl, trichloroacetyl), $C_1$–$C_6$ alkanoyl (e.g. formyl, acetyl), $C_4$–$C_8$ β-ketocarboxylic acyl (e.g. acetoacetyl), $C_2$–$C_{12}$ alkoxycarbonyl (e.g. t-butoxycarbonyl, cyclopropylmethoxycarbonyl, norbornyloxycarbonyl, 2,2,2-trichloroethoxycarbonyl), $C_8$–$C_{15}$ aralkoxycarbonyl (e.g. benzyloxycarbonyl, p-methoxybenzyloxycarbonyl, p-nitro- or p-methylbenzyloxycarbonyl, diphenylmethoxycarbonyl), and the like acyls] and ethers [including $C_1$–$C_6$ alkyl (e.g. methyl, t-butyl, cyclopropylmethyl, isobornyl, tetrahydropyranyl, methoxymethyl), $C_7$–$C_{15}$ aralkyl (e.g. benzyl, p-methoxy,- p-methyl- or p-nitrobenzyl, diphenylmethyl, trityl), and like groups]. The protecting group can preferably be introduced at the stage of Arylmalonic acid (III) or reactive derivatives thereof. The deprotection is carried out by e.g. 1) cleavage of acylates or ethers with an acid (e.g. mineral acid, Lewis acid, strong carboxylic acid, sulfonic acid), or base (e.g. sodium or potassium carbonate, hydroxide, organic base) at room temperature or elevated temperature if required in the presence of cation scavenger, or 2) hydrogenation of p-nitrobenzyloxycarbonyl or benzyl-oxycarbonyl with hydrogen and platinum or palladium by conventional manner.

When the carboxy at position 4 or of the side chain at position 7 or in Het is protected, the protecting group may be deprotected to give desired Compounds (I) in conventional manners for removing the protective groups. For example, 1) highly reactive esters, amides, and anhydrides are readily hydrolyzed with an acid or base; 2) 2-haloethyl, benzyl, methylbenzyl, nitrobenzyl, and diarylmethyl esters are cleaved by mild reduction (e.g. with tin, zinc, or divalent chromium salts in the presence of acids; sodium dithionite; catalytic hydrogenation with hydrogen over catalyst e.g. platinum, palladium, nickel); 3) benzyl, methoxybenzyl, methylbenzyl, dimethoxybenzyl, t-alkyl, trityl, diarylmethyl, and cyclopropylmethyl, esters are cleaved by the action of acids or by solvolysis [e.g. with mineral acids (e.g. hydrochloric acid), Lewis acids (e.g. aluminum chloride) sulfonic acids (e.g. toluene-p-sulfonic acid), strongly acidic carboxylic acids (e.g. trifluoroacetic acid, formic acid) if required in the presence of a cation acceptor e.g. anisole]; 4) phenacyl, ethynyl, p-hydroxy-3,5-di-t-butylbenzyl esters are cleaved by the action of base (e.g. alkali metal thiophenoxides, inorganic base, basic salts), and like methods.

Compounds (I) having one or more free carboxy can be converted into corresponding derivatives at the carboxy by introducing protective groups or substituents, by conventional methods (e.g. for esters, by the action of the corresponding alcohols with said condensing reagents, diazo compounds, haloformates, etc.; for salts, the action of alkali metal hydroxides, carbonates, or alkanoate salts, or the action of organic bases, ion-exchange resins).

Following preparations 1 through 5 are methods for making the starting materials of some examples. The nomenclature in each description is in accordance with that described in Japanese Patent Application (Open to Public Inspection No. 49-133,594) filed by Merck Inc., U.S.A.

Preparation 1(Preparation of 7α-amino compounds)

(1) To a solution of diphenylmethyl 7β-phenylacetamido-3-(1-methyltetrazol-5-yl)thiomethyl-1-oxadethia-3-cephem-4-carboxylate (955 mg) in methylene chloride (24 ml) are added phosphorous pentachloride (666 mg) and pyridine (0.258 ml) in nitrogen gas at −20° C. After stirring at −20° C for 30 minutes and at room temperature for 30 minutes, the mixture is mixed with methanol (12 ml) at −20° C and stirred at room temperature for 30 minutes. The reaction mixture is diluted with water (6 ml), stirred for 30 minutes and concentrated under reduced pressure. The residue is dissolved in 5% aqueous solution of sodium hydrogencarbonate under ice cooling, and extracted with ethyl acetate. The extract is washed with water, dried on sodium sulfate, and concentrated by filtration and washed with ether to yield diphenylmethyl 7β-amino-3-(1-methyltetrazol-5-yl)thiomethyl-1-oxadethia-3-cephem-4-carboxylate (661 mg). mp. 151–156° C. Yield: 86.5%.

IR: $\nu_{max}^{CHCl_3}$ 3420, 3345, 1790, 1718, 1630 cm$^{-1}$.

$\delta^{CDCl_3}$ 1.75brs2H, 3.81s3H, 4.28brs2H, 4.50d(4Hz)1H, 4.64brs2H, 4.98d(4Hz), 1H, 6.90s1H, 7.20–7.70mlOH.

UV: $\lambda_{max}^{(CH_3)_2SO}$ 286 nm ($\epsilon$=8695). $[\alpha]_D^{22.5}$ −232.8 ± 7.6° (c=0.360, (CH$_3$)$_2$SO).

2) In a procedure similar to that of above (1), diphenylmethyl 7β-phenylacetamido-3-(2-methyl-1,3,4-thiadiazol-5-yl)thiomethyl-1-oxadethia-3-cephem-4-carboxylate (381.5 mg) in methylene chloride (8 ml) is treated with phosphorous pentachloride (259 mg) and pyridine (0.1 ml) at −20° C, with methanol (8 ml), and with water (4 ml) to give diphenylmethyl 7β-amino-3-(2-methyl-1,3,4-thiadiazol-5-yl)thiomethyl-1-oxadethia-3-cephem-4-carboxylate (273.3 mg). Yield: 88.8%.

IR: $\nu_{max}^{CHCl_3}$ 3420, 3350, 1794, 1723 cm$^-$.

NMR: $\delta^{CDCl_3}$ 1.88s2H, 2.67s3H, 4.25+4.55ABq(14Hz)2H, 4.52 d(4Hz)1H, 4.68s2H, 5.00d(4Hz)1H, 7.07s1H.

(3) In a procedure similar to that of above (1), diphenylmethyl 7β-phenylacetamido-3-(1-t-butoxycarbonylmethyltetrazol-5-yl)thiomethyl-1-oxadethia-3-cephem-4-carboxylate (300 mg) in methylene chloride (10 ml) is treated with phosphorus pentachloride (180 mg) and pyridine (0.07 ml) at −20° C, with methanol (4 ml), and with water (4 ml) to give diphenylmethyl 7β-amino-3-(1-t-butoxycarbonylmethyltetrazol-5-yl)thiomethyl-1-oxadethia-3-cephem-4-carboxylate (189 mg). Yield: 76%.

IR: $\nu_{max}^{CHCl_3}$ 1795, 1753, 1722 cm$^{-1}$.

NMR: $\delta^{CDCl_3}$ 1.45s9H, 1.60-2.00m2H, 4.30s2H, 4.40-4.60mlH, 4.65brs2H, 4.86s2H, 5.00d(4Hz)1H, 6.95s1H.

Preparation 2 (Introduction of 7α-methoxy)

(1) A solution of diphenylmethyl 7β-amino-3-(1-methyltetrazol-5-yl)thiomethyl-1-oxadethia-3-cephem-4-carboxylate (600 mg) and 3,5-di-t-butyl-4-hydroxybenzaldehyde (353 mg) in a mixture of benzene (15 ml) and methylene chloride (5 ml) is refluxed for 1 hour while removing water by means of molecular sieve in a Dean Stark water-separator. The resulting solution of diphenylmethyl 7β-(3,5-di-t-butyl-4-hydroxybenzal)amino-3-(1-methyltetrazol-5-yl)thiomethyl-1-oxadethia-3-cephem-4-carboxylate is cooled at −10° C to −15° C, mixed with anhydrous magnesium sulfate (1 g) and then nickel peroxide (0.69 g) with stirring, and stirred at −10° C to −15° C for 30 minutes and at room temperature for 15 minutes. The reaction mixture is filtered, and the solid is washed with benzene. To the resulting solution of diphenylmethyl 7-(3,5-di-t-butyl-4-oxo-2,5-cyclohexadienylidenemethyl)imino-3-(1-methyltetrazol-5-yl)thiomethyl-1-oxadethia-3-cephem-4-carboxylate is added methanol (10 ml), and the solution is allowed to stand at room temperature for 1 hour, and concentrated to dryness under reduced pressure. The residue is chromatographed on silica gel (30 g) containing 10% water and eluted with a mixture of benzene and ethyl acetate (4:1) to give diphenylmethyl 7β-(3,5-di-t-butyl-4-hydroxybenzal)amino-7α-methoxy-3-(1-methyltetrazol-5-yl)thiomethyl-1-oxadethia-3-cephem-4-carboxylate (906 mg) as practically pure yellow foam. Yield: 99.7%.

(2) To a solution of the produce of above (1) in a mixture of methanol (10 ml) and tetrahydrofuran (5 ml) is added sodium salt of N-chloro-p-toluenesulfonamide (315 mg), and the mixture is stirred at room temperature for 1 hour, diluted with water, and extracted with methylene chloride. The extract is washed with water, dried or sodium sulfate, and evaporated to dryness under reduced pressure. The residue is purified by chromatography on silica gel (30 g) containing 10% water and eluted with a mixture of ethyl acetate: benzene;methylene chloride (1:1:1) to give diphenylmethyl 7β-amino-7α-methoxy-3-(1-methyltetrazol-5-yl)thiomethyl-1-oxadethia-3-cephem-4-carboxylate (469 mg). Over-all yield: 73.6%. mp. 160° – 162° C (decomposition).

IR: $\nu_{max}^{CHCl_3}$ 3425, 3350, 1792, 1724 cm$^{-1}$.

NMR: $\delta^{CDCl_3}$ 2.00brs2H, 3.38s3H, 3.87s3H, 4.32s2H, 4.73s2H, 4.92s1H, 7.00s1H.

As is seen in above (1), nickel peroxide worked well for the oxidation of the phenolic intermediate to give the 4-oxocyclohexadienylidene compound.

Preparation 3 (Preparation of Compound IV)

(1) To a solution of crude diphenylmethyl α-(4β-methylthio-3β-amino-2-oxoazetidin-1-yl)-α-isopropylideneacetate toluene-p-sulfonate salt (13.48 g) in methylene chloride (100 ml) is added a solution of chlorine in carbon tetrachloride (1.34 Mole/liter; 19.4 ml) at −78° C. The mixture is stirred at −78° C for 20 minutes and at 0° C for 20 minutes, and evaporated under reduced pressure. The residue is triturated thrice in a mixture of ether and petroleum ether, and evaporated to give crude diphenylmethyl α-[4β- and 4α-chloro-3β-amino-4-oxoazetidin-1-yl]-α-isopropylideneacetate toluene-p-sulfonate salt.

The product is treated with aqueous solution of sodium hydrogencarbonate and extracted with dichloromethane to give crude diphenylmethyl α-[4β- and 4α-chloro-3β-amino-2-oxoazetidin-1-yl]-α-isopropylideneacetate.

(2) To a solution of the product of above (1) (0.95 g) in a mixture of propargyl alcohol (3 ml) and tetrahydrofuran (2 ml) is added silver tetrafluoroborate (0.79 g), and the mixture is stirred at room temperature for 3 hours. The reaction mixture is diluted with benzene (50 ml), cooled to 0° C, and stirred with a mixture of 5% aqueous solution of sodium hydrogencarbonate (10 ml) and saturated saline (5 ml). The mixture is filtrated through a layer of Celite, and filtrate is separated. The benzene layer is dried over sodium sulfate, concentrated under reduced pressure to give brown heavy oil, and purified by chromatography on silica gel to give diphenylmethyl α-[4α- and 4β-propargyloxy-3β-amino-2-oxoazetidin-1-yl]-α-isopropylideneacetate in a ratio of about 1:1. The product is treated with α-diphenylmethoxycarbonyl-α-phenylacetyl chloride (1 mole equivalent) in methylene chloride in the presence of 2 mole equivalents of triethylamine and 1 mole equivalent of N,N-dimethylformamide to give diphenylmethyl α-[4β-propargyloxy-3β-(α-phenyl-α-diphenylmethoxycarbonylacetamido)-2oxoazetidin-1-yl]-α-isopropylideneacetate.

(3) To a solution of the product of above (2) (18.2g) in methanol (40 ml) is added a suspension of pre-reduced 5% palladium on calcium carbonate (3 g) in methanol (70 ml), and the mixture is hydrogenated under hydrogen atmosphere for 1 hour. After removing the catalyst by filtration, the reaction mixture is evaporated to give diphenylmethyl α-[4β-allyloxy-3β-(α-phenyl-α-diphenylmethoxycarbonylacetamido)-2-oxoazetidin-1-yl]-α-isopropylideneacetate.

(4) To a solution of the product obtained above (3) (8.6 g) in chloroform (70 ml) is gradually added a solution of m-chloroperbenzoic acid (2.8 g), and the mixture is kept at room temperature for 1 day. The reaction mixture is concentrated under reduced pressure. The obtained residue is dissolved in ethyl acetate, washed with 50% sodium sulfite, 5% sodium hydrogencarbonate in water, and saline, dried, and concentrated. The residue is purified by chromatography over silica gel to give diphenylmethyl α-[4β-(2,3-epoxypropoxy)-3β-(α-diphenylmethoxycarbonyl-α-phenylacetamido)-2-oxoazetidin-1-yl]-α-isopropylideneacetate.

(5) A solution containing lithium 1-methyl-1H-tetrazol-5-yl-mercaptide is prepared by mixing 1-methyl-5-mercapto-1H-tetrazole (2.8 g) in tetrahydrofuran (70 ml) with n-butyllithium (2.0 ml; 1.80 mole per liter hexane) under ice cooling and nitrogen atmosphere with stirring for 40 minutes. To this solution is added dropwise a solution of diphenylmethyl α-[4β-(2,3-epoxypropoxy)-3β-(α-phenyl-α-diphenylmethoxycarbonylacetamido)-2-oxoazetidin-1-yl]-α-isopropylideneacetate (15.8 g) in tetrahydrofuran (50 ml), and stirred for 5 hours at room temperature. The reaction mixture is diluted with methylene chloride, washed with ice cold hydrochloric acid and water, dried over sodium sulfate, and evaporated under reduced pressure. Purification of the residue by chromatography over silica gel gives diphenylmethyl α-{4β-[3-(1-methyltetrazol-5-ylthio)-2-hydroxypropoxy]-3β-(α-diphenylmethoxycarbonyl-α-phenylacetamido]-2-oxoazetidin-1-yl}-α-isopropylideneacetate.

(6) To a solution of the product of above (5) (21.0 g) in acetone (150 ml) is added Jone's reagent (13 ml), and the mixture is stirred for 0.5 hours at room temperature. After adding methanol at 0° C, the reaction mixture is diluted with ethyl acetate to separate inorganic solid which is filtered off, and washed with water. Combined filtrate and washings are washed with water, dried over sodium sulfate, and evaporated under reduced pressure. Purification of the residue by chromatography on silica gel gives diphenylmethyl α-{4β-[3-(1-methyltetrazol-5-yl)thio-2-oxopropoxy]-3β-(α-diphenylmethoxycarbonyl-α-phenylacetamido)-2-oxoazetidin-1-yl}-α-isopropylideneacetate.

(7) To a solution of the product of above (6) (7.5 g) in methylene chloride (95 ml) is bubbled ozone at −78° C until the mixture shows blue color. To the solution is added dimethyl sulfide (7 ml), warmed to room temperature, washed with water, dried over sodium sulfate, and evaporated to give diphenylmethyl α-{4β-[3-(1-methyltetrazol-5-yl)thio-2-oxopropoxy]-3β(α-diphenylmethoxycarbonyl-α-phenylacetamido)-2-oxoazetidin-1-yl}-α-isopropylideneacetate.

(8) To a solution of the product of above (7) (3.10 g) in methylene chloride (10 ml) is added acetic acid (10 ml), water (15 ml), and zinc powder (4.0 g) under ice cooling, and the mixture is stirred for 1 hour at the same temperature. The solid material is filtrated off from the reaction mixture which is washed with water, dried over sodium sulfate, and evaporated to give diphenylmethyl α-{4β-[3-(1-methyltetrazol-5-yl)thio-2-oxopropoxy]-3β-(α-diphenylmethoxycarbonyl-α-phenylacetamido)-2-oxoazetidin-1-yl}-α-hydroxyacetate.

(9) To a solution of the product of above (8) (2.4 g) in methylene chloride (30 ml) is added thionyl chloride (0.3 ml) and pyridine (0.20 ml) under nitrogen and ice cooling. After stirring for 30 minutes at the same temperature, the mixture is poured into ice water, and extracted with ethyl acetate. The extract solution is washed with water, dried over sodium sulfate, and evaporated to give diphenylmethyl α-{4β-[3-(1-methyltetrazol-5-yl)thio-2-oxopropoxy]-3β-(α-diphenylmethoxycarbonyl-α-phenylacetamido)-2-oxoazetidin-1-yl}-α-chloroacetate.

(10) To a solution of the product of above (9) (4.8 g) in methylene chloride (40 ml) is added triphenylphosphine (4.0 g), and the mixture is refluxed under nitrogen atmosphere for 2 hours. After cooling, the reaction mixture is poured into aqueous 2% sodium hydrogencarbonate solution, and is extracted with methylene chloride. The extract solution is dried over sodium sulfate, and evaporated under reduced pressure. Purification of the residue by silica gel chromatography gives diphenylmethyl α-{4β-[3-(1-methyltetrazol-5-yl)thio-2-oxopropoxy]-3β-(α-diphenylmethoxycarbonyl-α-phenylacetamido)-2-oxoazetidin-1-yl}-α-triphenylphosphoranylideneacetate, the starting material of Example I-1.

Preparation 4

(1) A solution of the product of Preparation 3 (4) (5.8 g) in methylene chloride (70 ml) cooled at −30° C are added t-butyl hypochlorite (2 ml) and a solution of lithium methoxide in methanol over a period of 10 minutes, and the mixture is stirred for 2 minutes. The mixture is then mixed with 0.5 ml of acetic acid, poured into ice water, 5% sodium thiosulfate, water, and aqueous sodium chloride, dried, and evaporated to give diphenylmethyl α-[4β-(2,3-epoxypropoxy)-3β-(α-diphenylmethoxycarbonyl-α-phenylacetamido)-3α-methoxy-2-oxoazetidin-1-yl]-α-isopropylideneacetate.

(2) The product of above (1) is treated with lithium 1-methyl-1H-tetrazol-5-ylmercaptide (1.2 mole equivalents) in tetrahydrofuran at room temperature for 3 hours to give diphenylmethyl α-{β-[3-(1-methyltetrazol-5-yl)thio-2-hydroxypropoxy]-3β-(α-diphenylmethoxycarbonyl-α-phenylacetamido)-3α-methoxy-2-oxoazetidin-1-yl}-α-isopropylideneacetate.

(3) The product of above (2) is treated with 2.2 mole equivalent of Jones reagent in acetone at room temperature for 60 minutes to give diphenylmethyl α-{4β-[3-(1-methyltetrazol-5-yl)thio-2-oxopropoxy]-3β-(α-diphenylmethoxycarbonyl-α-phenylacetamido)-3α-methoxy-2-oxoazetidin-1-yl}-α-isopropylideneacetate.

(4) The product of above (3) is dissolved in methylene chloride, and ozone is bubbled therein at −78° C. The mixture is mixed with acetic and and 5 weights of zinc at 0° C and stirred for 2 hours to give diphenylmethyl α-{4β-[3-(1-methyltetrazol-5-yl)thio-2-oxopropoxy]-3β-(α-diphenylmethoxycarbonyl-α-phenylacetamido)-3α-methoxy-2-oxoazetidin-1-yl}-α-hydroxyacetate.

(5) The product of above (4) is treated with thionyl chloride (1.2 mole equivalents) and pyridine (1.2 mole equivalents) in methylene chloride at 0° C for 20 minutes to give diphenylmethyl α-{4β-[3-(1-methyltetrazol-5-yl)thioacetonyloxy]-3β-(α-diphenylmethoxycarbonyl-α-phenylacetamido)-3α-methoxy-2-oxoazetidin-1-yl}-α-chloroacetate.

(6) The product of above (5) is treated with triphenylphosphine (1.5 mole equivalents) in methylene chloride at refluxing temperature under nitrogen for 2 hours to give the starting material of Example I-2, diphenylmethyl α-{4β-[3-(1-methyltetrazol-5-yl)thioacetonyl]oxy-3β-(α-diphenylmethoxycarbonyl-α-phenylacetamido)-3α-methoxy-2-oxoazetidin-1-yl}-α-triphenylphosphoranylideneacetate.

Preparation 5

(1) To a solution of diphenylmethyl α-[4α- and 4β-propargylpoxy-3β-amino-2-oxoazetidin-1-yl]-α-isopropylideneacetate, prepared by the method of Preparation 3 (1and (2), in methylene chloride is added 1.1 mole equivalent of α-p-benzyloxyphenyl-α-diphenyl-methoxycarbonylacetyl chloride in the presence of 1.1 mole equilvant of pyridine to give diphenylmethyl α-[4α- and 4β-propargyloxy-3β-(α-p-benzyloxyphenyl-α-diphenylmethoxycarbonylacetamido)2-oxoazetidin-1-yl]-α-isopropylideneacetate, which is separated to give 4β-propargyloxy isomer.

(2) The product of above (1) is hydrogenated over palladium on calcium carbonate in ethanol at room temperature over 2 hours to give diphenylmethyl α-[4β-allyloxy-3β-(α-p-benzyloxyphenyl-α-diphenylmethoxycarbonylacetamido)-2-oxoazetidin-1-yl]-α-isopropylideneacetate.

(3) The product of above (2) in methylene chloride is mixed with t-butyl hypochlorite and lithium methoxide in methanol, and the mixture stirred at −30° C for 15 minutes to give diphenylmethyl α-[4β-allyloxy-3β(α-p-benzyloxyphenyl-α-diphenylmethoxycarbonylacetamido)-3α-methoxy-2-oxoazetidin-1-yl]-α-isopropylideneacetate.

(4) The product of above (3) is epoxidized with 1.1 mole equivalent of m-chloroperbenzoic acid in methylene chloride at room temperature for 2 days to give diphenylmethyl α-[4β-(2,3-epoxypropoxy)-3β-(α-p-benzyloxyphenyl-α-diphenylmethoxycarbonylacetamido)-3α-methoxy-2-oxoaxetidin-1-yl]-α-isopropylideneacetate.

(5) The product of above (4) is treated with lithium 1-methyl-1H-tetrazol-5-ylmercaptide (1.2 mole equivalents) in tetrahydrofuran at room temperature for 2 hours to give diphenylmethyl α-{4β-[3-(1-methyltetrazol-5-yl)thio-2-oxopropoxy]-3β-(α-p-benzyloxyphenyl-α-diphenylmethyoxycarbonylacetamido)-3α-methoxy-2-oxoazetidin-1-yl}-α-isopropylideneacetate.

(6) The product of above (5) is oxidized with 3 mole equivalents of Jones reagent at room temperature for 30 minutes to give diphenylmethyl α-{4β-[3-(1-methyltetrazol-5-yl)thio-2-oxopropoxy]-3β-(α-p-benzyloxyphenyl-α-diphenylmethoxycarbonylacetamido)-3α-methoxy-2-oxoazetidin-1-yl}-α-ispropylideneacetate.

(7) The product of above (6) is treated with ozone in methylene chloride at −78° C, followed by acetic acid and zinc (5 weights) to give diphenylmethyl α-{4β-[3-(1-methyltetrazol-5-yl)thio-2-oxopropoxy]-3β-(α-p-benzxyloxyphenyl-α-diphenylmethoxycarbonylacetamido)-3α-methoxy-2-oxoazetidin-1-yl}-α-hydroxyacetate.

(8) The product of above (7) is treated with thionyl chloride (1.2 mole equivalents) and pyridine (1.2 mole equivalents) in methylene chloride at 0° C for 30 minutes to give diphenylmethyl α-{4β-[3-(1-methyltetrazol-5-yl)thio-2-oxopropoxy]-3β-(α-p-benzyloxyphenyl-α-diphenylmethoxycarbonylacetamido)-3α-methoxy-2-oxoazetidin-1-yl{-α-chloroacetate.

(9) The product of above (8) is refluxed in methylene chloride in the presence of triphenylphosphine (1.5 mole equivalents) under nitrogen for 5 hours to give the starting material of Example I-3, diphenylmethyl α-{3β-(α-p-benzyloxyphenyl-α-diphenylmethoxycarbonylacetamido)-3α-methoxy-4β-[3-(1-methyltetrazol-5-yl)thio-2-oxopropoxy]-2-oxoazetidin-1-yl}-α-triphenylphosphoranylideneacetate.

TABLE I

Minimal inhibitory concentration of ArCHCONH-[structure]-COB, CH$_2$SHet (μg/ml) as sodium salt at an inoculum size of $10^8$ (pH 7.0) (The ester is assayed in the presence of 5% horse serum)

| Example No. | III-8 | III-11 | III-9 | III-1 | III-2 | III-12 | III-10 | III-6 |
|---|---|---|---|---|---|---|---|---|
| Ar | [thienyl] | [thienyl] | [thienyl] | C$_6$H$_5$— | C$_6$H$_5$— | C$_6$H$_5$— | C$_6$H$_5$— | HO—[phenyl]— |
| Het | T | A | T | T | T | Z | A | T |
| B | OH | OH | OH | OH | 5-indanyl | OH | OH | OH |
| *Escherichia coli* H | 0.1 | 0.78 | 0.1 | 0.1 | 0.1 | 0.2 | 0.78 | 0.2 |
| *E. coli* JC-2 | 0.1 | 12.5 | 0.1 | 0.2 | 0.2 | 0.39 | 3.13 | 0.39 |
| *E. coli* 377 | 0.2 | 6.25 | 0.2 | 0.2 | 0.2 | 0.78 | 0.25 | 0.39 |
| *E. coli* 73 | > | > | > | > | > | > | > | > |
| *Serratia marsescens* 13880 | 0.78 | 25 | 0.78 | 0.78 | 0.78 | 1.56 | 50 | 0.78 |
| *Klebsiella pneumoniae* | 0.1 | 3.13 | 0.2 | 0.2 | 0.2 | 0.78 | 3.13 | 0.78 |
| K. 363 | > | > | > | — | > | > | > | > |
| *Enterobacter cloacae* 233 | 0.2 | 25 | 0.39 | 0.39 | 0.39 | 1.56 | 12.5 | 0.78 |
| *Proteus mirabilis* PR-4 | 0.2 | 1.56 | 0.39 | 0.39 | 0.39 | 0.39 | 0.78 | 0.78 |
| *P. morganii* No. 9 | 0.39 | 1.56 | 0.39 | 0.39 | 0.39 | 0.39 | 0.78 | 0.78 |
| *P. vulgaris* No. 3 | — | — | — | — | — | — | — | > |
| *P. vulgaris* CN-329 | 50 | > | 100 | 100 | 50 | 100 | > | > |
| *Pseudomonas aeruginosa* Denken | > | > | > | > | > | > | > | > |
| *Ps. aeruginosa* 25619 | 3.13 | > | 6.25 | 3.13 | 6.25 | 3.13 | 100 | 6.25 |
| *Ps. aeruginosa* 24 | > | — | — | > | > | > | > | > |

(Abbreviations)
T: 1-methyltetrazol-5-yl;
A: 1-carboxymethyltetrazol-5-yl;
Z: 2-methyl-1,3,4-thiadiazol-5-yl.
>: higher than 100 μg/ml.

TABLE II

Minimal inhibitory concentration of ArCHCONH-[structure]-COB, OCH$_3$, CH$_2$SHet (μg/ml) as sodium salt at an inoculum size of $10^8$ (ph 7.0) (The esters are assayed in the presence of 5% horse serum)

| Example No. | III-23 | III-19 | III-13 | III-24 | III-15 | III-16 | III-14 CH$_3$COO | III-25 H$_2$NCOO | III-27 H$_2$NCONHCO |
|---|---|---|---|---|---|---|---|---|---|
| Ar | [thienyl] | [thienyl] | [phenyl] | [phenyl] | HO—[phenyl]— | HO—[phenyl]— | [phenyl] | [phenyl] | [phenyl] |
| Het | T | T | T | T | T | T | T | T | T |
| B | OH | OH | OH | 5-indanyl | OH | OH | OH | OH | OH |
| *Escherichia coli* H | 0.025 | 0.025 | 0.025 | 0.025 | 0.1 | 0.1 | 0.2 | 0.1 | 0.05 |
| *E. coli* JC-2 | 0.05 | 0.05 | 0.1 | 0.1 | 0.2 | 0.2 | 0.39 | 0.39 | 0.2 |
| *E. coli* 377 | 0.39 | 0.1 | 0.02 | 0.78 | 0.39 | 0.2 | 1.56 | 0.78 | 0.78 |
| *E. coli* 73 | 0.2 | 0.2 | 0.39 | 0.39 | 0.78 | 0.78 | 1.56 | 1.56 | 0.78 |
| *Serratia marsescense* 13880 | 0.39 | 0.39 | 0.39 | 0.78 | 1.56 | 0.39 | — | 1.56 | 3.13 |
| *Klebsiella Pneumoniae* | 0.05 | 0.2 | 0.1 | 0.1 | 0.2 | 0.2 | 0.39 | 0.39 | 0.39 |
| *Klebsiella sp.* 363 | 0.1 | 0.05 | 0.05 | 0.05 | 0.1 | 0.2 | 0.78 | 0.39 | 0.2 |
| *Enterobacter cloacea* 233 | 0.2 | 0.1 | 0.2 | 0.2 | — | 0.39 | 0.78 | 0.78 | 0.78 |
| *Proteus mirarbilis* PR-4 | 0.1 | 0.2 | 0.2 | 0.2 | 0.1 | 0.39 | 0.39 | 0.2 | 0.39 |
| *P. Morganii* No. 9 | 0.1 | 0.1 | 0.1 | 0.2 | 0.39 | 0.2 | 0.39 | 0.39 | 0.39 |
| *P vulgaris* No. 3 | — | 0.2 | 0.2 | 0.39 | 0.39 | 0.39 | 0.39 | 0.39 | 0.39 |
| *P. vulgaris* CN-329 | 0.1 | 0.1 | 0.1 | 0.1 | 0.39 | 0.78 | 0.2 | 0.2 | 0.2 |
| *Pseudomonas aeruginosa* Denken | 100 | 100 | 100 | 100 | 100 | 100 | > 25 | > 25 | > 12.5 |
| *Ps. aeruginosa* 25619 | 12.5 | 12.5 | 12.5 | 12.5 | 6.25 | 12.5 | 25 | 25 | 50 |
| *Ps. aeruginosa* 24 | 50 | 50 | 50 | 50 | 50 | 25 | 100 | 100 | 50 |

(Abbreviations)
T: 1-methyltetrazol-5-yl;
>: higher than 100 μg/ml.

TABLE III

Minimal inhibitory concentrating of the reference compounds as sodium salts at an inoculum size of $10^8$ (pH 7.0) (μg/ml)

| Compound No. (Optically pure) | (1) | (2) | (3) | (4) | Cefalotin | Cefazolin |
|---|---|---|---|---|---|---|
| *Escherichia coli* H | > | 0.39 | 1.56 | 0.1 | 3.2 | 1.6 |
| *E. coli* JC-2 | > | 6.25 | 1.56 | 0.2 | 12.5 | 3.2 |
| *E. coli* 377 | > | > | 25 | 50 | > | 100 |
| *E. coli* 73 | > | > | > | > | > | > |
| *Serratia marsescens* 13880 | > | > | > | 100 | > | > |

TABLE III-continued

Minimal inhibitory concentrating of the reference compounds as sodium salts at an inoculum size of $10^8$ (pH 7.0) (μg/ml)

| Compound No. (Optically pure) | (1) | (2) | (3) | (4) | Cefalotin | Cefazolin |
|---|---|---|---|---|---|---|
| *Klebsiella pneumoniae* | > | 1.56 | 3.13 | 0.2 | 1.6 | 3.2 |
| *Klebsiella* 363 | > | > | > | > | > | > |
| *Enterobactor cloacea* 233 | > | > | > | > | > | > |
| *Proteus mirabilis* PR-4 | > | 1.56 | 1.56 | 0.2 | 3.2 | 6.2 |
| *P. morganii* No. 9 | > | > | 50 | 100 | > | > |
| *P. vulgaris* No. 3 | — | — | — | — | > | > |
| *P. vulgaris* CN-329 | > | > | > | > | > | > |
| *Pseudomonas aeruginosa* Denken | > | > | > | > | > | > |
| *Ps. aeruginosa* 25619 | > | > | > | > | > | > |
| *Ps. aeruginosa* 24 | > | > | > | > | > | > |

*) Compound No.
(1): 7β-(α-phenylglycinamido)-3-methyl-1-oxadethia-3-cephem-4-carboxylic acid.
(2): 7β-(2-thienylacetamido)-1-oxadethiacephalosporanic acid.
(3): 7β(1-tetrazolyl)acetamido-3-(2-methyl-1,3,4-thiadiazol-5-yl)thiomethyl-1-oxadethia-3-cephem-4-carboxylic acid.
(4): 7β-mandelamido-3-(1-methyltetrazol-5-yl)thiomethyl-1-oxadethia-3-cephem-4-carboxylic acid.
>: higher than 100 μg/ml.

The following examples are provided to illustrate this invention in detail. The elemental analyses and physical constants of the products in each example are consistent with the given structure. In the following examples, the products usually contain a nearly equal amount of isomers at α-asymmetric carbon in the amide side chain. Both of the isomers are included in the scope of this invention, and, if necessary, are separable by the chromatographic technics or other conventional methods.

The nomenclature in each description is in accordance with that described in Japanese Patent Application (OPI No. 49-133,594).

I. RING FORMATION

Example I-1

A solution of diphenylmethyl α-[4β-(1-methyltetrazol5-yl)thioacetonyloxy-3β-(α-phenyl-α-diphenylmethoxycarbonylacetamideo)-2-oxoazetidin-1-yl]-α-triphenylphosphoranylideneacetate (650 mg) in dioxane (5 ml) is refluxed in nitrogen atmosphere for 16 hours. The reaction mixture is concentrated under reduced pressure. The residue is purified by chromatography on silica gel (20 g) containing 10% water, and eluted with a mixture of benzene and ethyl acetate (4 : 1) to give diphenylmethyl 7β-(α-phenyl-α-diphenylmethoxycarbonylacetamido)-3-(1-methyltetrazol-5-yl)thiomethyl-1-oxadethia-3-cephem-4-carboxylate (432 mg). mp. 107° – 109° C. Yield: 80%.

IR: $\nu_{max}^{KBr}$ 3410, 1793, 1719, 1694, 1630, 1600 cm$^{-1}$.

Example I-2

In a procedure similar to that described in Example I-1, diphenylmethyl α-[4β-(1-methyltetrazol-5-yl)thioacetonyloxy-3β-(α-phenyl-α-diphenylmethoxycarbonylacetamido)-3α-methoxy-2-oxoazetidin-1-yl]-α-triphenylphosphoranylideneacetate (543 mg) is refluxed in dioxane (5 ml) for 15 hours in nitrogen gas, and purified by chromatography on silica gel (15 g) to give diphenylmethyl 7β-(α-diphenylmethoxycarbonyl-α-phenylacetamido)-7α-methoxy-3-(1-methyltetrazol-5-yl)thiomethyl-1-oxadethia-3-cephem-4-carboxylate (540 mg). Yield: 67%.

Example I-3

In a procedure similar to that of Example I-2, diphenylmethyl α-[3β-(α-p-benzyloxyphenyl-α-diphenylmethoxycarbonylacetamido)-3α-methoxy-4β-[3-(1-methyltetrazol-5-yl)thio-2-oxopropoxy]-2-oxoazetidin-1-yl]-α-triphenylphosphoranylideneacetate is refluxed on silica gel to give diphenylmethyl 7β-(α-p-benzyloxyphenyl-α-diphenylmethoxycarbonylacetamido)-7α-methoxy-3-(1-methyltetraxol-5-yl)thiomethyl-1-oxadethia- 3-cephem-4-carboxylate.

II. AMIDE FORMATION

Example II-1

To a stirred solution of diphenylmethyl 7β-amino-3-(1-methyltetrazol-5-yl)thiomethyl-1-oxadethia-3-cephem-4-carboxylate (192 mg) in tetrahydrofuran (2 ml) and acetone (1 ml) are added mono-diphenylmethyl phenylmalonate (208 mg) and N-ethoxycarbonyl-2-ethoxy-1,2-dihydroquinoline (148 mg) at 0° C, and then the mixture is allowed to stand at room temperature overnight. The reaction mixture is diluted with ethyl acetate, washed with 2N-hydrochloric acid, water, 5% aqueous solution of sodium hydrogencarbonate, and then water, dried on sodium sulfate, and evaporated to dryness. The residue is purified by chromatography on silica gel (20 g) containing 10% water and eluted with a mixture of benzene and ethyl acetate (4 : 1). The crystals obtained from the fraction are washed with a mixture of ether and n-pentane to give diphenylmethyl 7β-(α-phenyl-α-diphenylmethoxycarbonylacetamido)-3-(1-methyltetrazol-5-yl)thiomethyl-1-oxadethia-3-cephem-4-carboxylate, mp. 100° – 105° C.

Yield: 40%.

IR: $\nu_{max}^{CHCl_3}$ 1800, 1720, 1680 cm$^{-1}$.

NMR: $\delta^{CDCl_3}$ 7.00s1H, 6.95s1H, 5,80dd(4;9Hz)1H, 5.06d(4Hz)1H, 4.75s1H, 4.65brs2H, 4.33s2H, 3.86s3H.

By using α-(diphenylmethoxycarbonyl-α-phenyl)acetyl chloride, triethylamine hydrochloride, and pyridine instead of mono-diphenylmethyl phenylmalonate and N-ethoxycarbonyl-2-ethoxy-1,2-dihydroquinoline, the reaction is analogously carried out for 25 minutes to give the same product as mentioned above in 99% yield. mp. 107° – 109° C.

IR: $\nu_{max}^{KBr}$ 3410, 1793, 1719, 1694, 1630, 1600 cm$^{-1}$.
UV: $\lambda_{max}^{(CH_3)_2SO}$ 281 nm (ε = 10136).

NMR: $\delta^{(CD_3)_2SO}$ 3.84s3H, 4.30brs2H, 4.58brs2H, 4.69s1H/2, 4.71s1H/2, 5.02d(4Hz)1H, 5.76dd(4;9Hz)1H, 6.86brs1H, 6.90brs1H, 7.0 - 7.5m20H, 7.76d(9)1H, $[\alpha]_D^{23}$ − 144.2 ± 8.1° (c = 0.226, (CH$_3$)$_2$SO)

Example II-2

To a stirred solution of diphenylmethyl 7β-amino-3-(1-methyltetrazol-5yl)thiomethyl-1-oxadethia-3-cephem-4-carboxylate (500 mg) in methylene chloride (20 ml) are added pyridine (0.1 ml) and a solution of α-(p-nitrobenzyloxycarbonyl)-α-phenylacetyl chloride (510 mg) in methylene chloride (2 ml) under ice - cooling in nitrogen atmosphere, and the mixture is stirred for 25 minutes. The reaction mixture is poured into water, and extracted with methylene chloride. The extract is dried on sodium sulfate and evaporated to dryness to yield residue (1.04 g) which is chromatographed on silica gel (40 g) containing 10% water, eluted with a mixture of benzene and ethyl acetate (4 : 1), and crystallized from a mixture of ethyl acetate and ether to give diphenylmethyl 7β-(α-p-nitrobenzyloxycarbonyl-α-phenylacetamido)-3-(1-methyltetrazol-5-yl)thiomethyl-1-oxadethia-3-cephem-4-carboxylate (670 mg), mp. 122° - 125° C. Yield: 83%.

UV: $\lambda_{max}^{(CH_3)_2SO}$ 278 nm ($\epsilon$ = 18490).

IR: $\nu_{max}^{KBr}$ 3400, 3340, 1792, 1742, 1718, 1680, 1631, 1604, 1520, 1345 cm$^{-1}$.

NMR $\delta^{(CD_3)_2SO}$ 3.88s3H/2, 3.89s3H/2, 4.24brs2H, 4.65brs2H, 5.05s1H, 5.20d(4Hz)1H, 5.32brs2H, 5.75m1H, 6.86s1H, 7.20 - 7.70m15H, 7.50 - 8.0A$_2$X$_2$4H.

$[\alpha]_D^{22.5}$ − 150.6 ± 5.4° (c = 0.350, (CH$_3$)$_2$SO).

Example II-3

To a stirred solution of diphenylmethyl 7β-amino-3-(1-methyltetrazol-5-yl)thiomethyl-1-oxadethia-3-cephem-4-carboxylate (100 mg) in methylene chloride (11 ml) are added pyridine (21 mg) and a solution of α-(indan-5-yl)oxycarbonyl-α-phenylacetyl chloride (prepared from the corresponding acid (77 mg)) in methylene chloride (2 ml) under ice cooling, and the mixture is stirred for 30 minutes. The reaction mixture is poured into a mixture of ethyl acetate and water, and the organic layer is taken up. This is washed with diluted hydrochloric acid, aqueous solution of sodium hydrogencarbonate, water, and aqueous solution of sodium chloride, dried on magnesium sulfate, and evaporated to dryness. The residue is purified by chromatography on silica gel (5.5 g) containing 10% water, and eluted with a mixture of benzene and ethyl acetate (4 : 1) to give diphenylmethyl 7β-[α-(5-indanyl)oxycarbonyl-α-phenylacetamido]-3-(1-methyltetrazol-5yl)thiomethyl-1-oxadethia-3-cephem-4-carboxylate (144 mg) as pale yellow foam. Yield: 95.4%. IR: $\nu_{max}^{CHCl_3}$ 1800, 1735, 1685 cm$^{-1}$.

Example II-4

To a solution of diphenylmethyl 7β-amino-3-(1-methyltetrazol-5-yl)thiomethyl-1-oxadethia-3-cephem-4-carboxylate (144 mg) in methylene chloride (4 ml) are added pyridine (0.048 ml) and a solution of phenylmalonyl hemichloride in methylene chloride (2 ml) (prepared by reacting phenylmalonic acid (108 mg) with thionyl chloride (0.048 ml) in a mixture of ether (1 ml) and dimethylformamide (2 drops) at room temperature for 20 hours) and the mixture is kept at 0° C for 20 minutes. The reaction mixture is diluted with ethyl acetate, washed with dilute hydrochloric acid and water, dried on sodium sulfate, and concentrated. The residue is purified by chromatography on silica gel containing 10% water, and eluted with a mixture of ethyl acetate and benzene (1 : 1 to 1 : 0) to give diphenylmethyl 7β-(α-carboxy-α-phenylacetamido)-3-(1-methyltetrazol-5-yl)thiomethyl-1-oxadethia-3-cephem-4-carboxylate (107 mg). Yield: 61%.

Example II-5

To a solution of 7β-amino-3-(1-methyltetrazol-5-yl)thiomethyl-1-oxadethia-3-cephem-4-carboxylic acid (78 mg) and triethylamine (0.036 ml) in methylene chloride (1 ml) is added a solution of phenylmalonyl monochloride monobenzhydryl ester in methylene chloride (2 ml) [prepared by reacting monobenzhydryl phenylmalonate (60 mg) with thionyl chloride (0.04 ml) in a mixture of ether (1 ml) and dimethylformamide (1 drop) at room temperature for 10 hours]. and the mixture is kept at 0° C for 1 hour. The reaction mixture is diluted with a mixture of ethyl acetate and acetic acid (9 : 1) to give 7β-(α-diphenylmethoxycarbonyl-α-phenylacetamido)-3-(1-methyltetrazol-5-yl)thiomethyl-1-oxadethia-3-cephem-4-carboxylic acid (60 mg).

Example II-6

To a solution of 7β-amino-3-(1-methyltetrazol-5-yl)thiomethyl-1-oxadethia-3-cephem-4-carboxylic acid (78 mg) and triethylamine (0.036 ml) in methylene chloride (1 ml) is added a solution of phenylchloroformylketone (45 mg) in methylene chloride (0.5 ml), and the mixture is kept at 0° C for 2 hours. The reaction mixture is washed with water, dried, and evaporated. The residue is dissolved in ethyl acetate, purified by chromatography on silica gel (10 g) containing 10% water, and eluted with a mixture of ethyl acetate and acetic acid (9 : 1) to yield 7β-(α-phenyl-α-carboxyacetamido)-3-(1-methyltetrazol-5-yl)thiomethyl-1-oxadethia-3-cephem-4-carboxylic acid (88 mg). Yield: 74%.

Example II-7

A solution of diphenylmethyl 7β-amino-3-(1-methyltetrazol-5-yl)thiomethyl-1-oxadethia-3-cephem-4-carboxylate (96 mg) in methylene chloride (3 ml) is added to a solution of a mixed anhydride [prepared by reacting mono-t-butyl p-hydroxyphenylmalonate (76 mg) with i-butyl chlorformate (0.037 ml) in the presence of triethylamine (0.0416 ml) in methylene chloride (4 ml) at −30° C for 30 minutes and at 0° C for 10 minutes], and the mixture is stirred at −30° C for 30 minutes, at 0° C for 2 hours, and at room temperature for 30 minutes. The reaction mixture is concentrated under reduced pressure. The residue is dissolved in a mixture (2 ml) of pyridine and water (7 : 3), and stirred at room temperature for 1 hour. The reaction mixture is poured into ice-water, and extracted with ethyl acetate. The extract is washed with water, 2N-hydrochloric acid, water, 5% aqueous solution of sodium hydrogen carbonate, and water, dried on sodium sulfate, and concentrated under reduced pressure. The residue (148 mg) is purified by chromatography on silica gel (15 g) containing 10% water and eluted with a mixture of benzene and ethyl acetate (4 : 1). The eluate is triturated in a mixture of ether and pentane to give diphenylmethyl 7β-(α-p-hydroxyphenyl-α-t-butoxycarbonylacetamido)-3-(1-methyltetrazol-5-yl)thiomethyl-1-oxadethia-3-cephem-4-carboxylate (66 mg).

mp. 124 - 126° C. Yield: 46%.

IR: $\nu_{max}^{CHCl_3}$3410, 3320, 1800, 1717, 1679, 1510 cm$^{-1}$.

NMR: $\delta^{CDCl_3}$ 1.40s9H, 3.80s3H, 4.27brs2H, 4.38s1H/2, 4.42s1H/2, 4.62brs2H, 5.04d(4Hz)1H, 5.70m17&;10Hz)1H, 6.46 - 8.31mlH.

Example II-8

To a suspension of α-p-hydroxyphenylmalonic acid monobenzhydryl ester (507 mg) in methylene chloride (3 ml) are added triethylamine (139 μl) and oxalyl chloride (85 μl) at 0° C. After stirring for 45 minutes at 0° C, the mixture is added to a solution of diphenylmethyl 7β-amino-3-(1-methyltetrazol-5-yl)-thiomethyl-1-oxadethia-3-cephem-4-carboxylate (191 mg) in methylene chloride (3 ml) and pyridine (80 μl) at 0° C. After stirring for 30 minutes at 0° C, the reaction mixture is diluted with ethyl acetate, washed with the 2N-hydrochloric acid, water, 5% sodium hydrogencarbonate aqueous solution, and water, dried on sodium sulfate, and concentrated under reduced pressure. The residue is chromatographed on silica gel (15 g) containing 10% water, and eluted with a mixture of benzene and ethyl acetate (9 : 1) to give diphenylmethyl 7β-[α-p-hydroxyphenyl-α-diphenylmethoxycarbonylacetamido]-3-(1-methyltetrazol-5-yl)-thiomethyl-1-oxadethia-3-cephem-4-carboxylate as colorless foam (137 mg). Yield: 41.6%.

IR: $\nu_{max}^{CHCl_3}$ 3325, 1798, 1722, 1679 cm$^{-1}$.

NMR: $\delta^{CDCl_3}$ 3.73s3H, 4.20brs2H, 4.53brs2H, (4.60s + 4.63s)1H, 4.93brd(4Hz)1H, 5.47 – 5.77m1H.

Example II-9

To a solution of diphenylmethyl 7β-amino-3-(1-methyltetrazol-5-yl)thiomethyl-1-oxadethia-3-cephem-4-carboxylate (96 mg) in a mixture of tetrahydrofuran (1 ml) and acetone (0.5 ml) are added mono-t-butyl α-(2-thienyl)malonate (129 mg) and 1-ethoxycarbonyl-2-ethoxy-1,2-dihydroquinoline (132 mg) in four equal portions at 1 hour intervals with stirring at room temperature in nitrogen gas, and the mixture is stirred for 1 hour. The reaction mixture is diluted with ethyl acetate, washed with 2N-hydrochloric acid, water, 5% aqueous sodium hydrogencarbonate, and water, dried on sodium sulfate, and concentrated under reduced pressure. The residue (251 mg) is purified by chromatography on silica gel (10 g) containing 10% water, and eluted with a mixture of benzene and ethyl acetate (4 : 1). The eluate is triturated with a mixture of ether and pentane to give diphenylmethyl 7β-[α-(2-thienyl)-α-t-butyoxycarbonylacetamido]-3-(1-methyltetrazol-5-yl),thiomethyl-1-oxadethia-3-cephem-4-carboxylate as amorphous powder (49 mg). mp. 97 – 99° C. Yield: 34.8%.

IR: $\nu_{max}^{CHCl_3}$ 3400, 1800, 1720, 1690, 1511 cm$^{-1}$.

NMR: $\delta^{CDCl_3}$ 1.47s9H, 3.93s3H, 4.32s2H, 4.69brs2H, 4.80brs1H, 5.09d(4Hz)1H, 5.75dd(10;4Hz)1H, 6.90 – 7.73m15H.

Example II-10

To a solution of diphenylmethyl 7β-amino-3-(1-methyltetrazol-5-yl)thiomethyl-1-oxadethia-3-cephem-4-carboxylate (96 mg) in a mixture of tetrahydrofuran (1 ml) and acetone (0.5 ml) are added mono-t-butyl α-(3-thienyl)malonate (132 mg) and 1-ethoxycarbonyl-2-ethoxy-1,2-dihydroquinoline (132 mg) under ice-cooling, and the mixture is stirred at room temperature for 4 hours. The reaction mixture is diluted with ethyl acetate, washed with water, 1N-hydrochloric acid, water, 5% aqueous solution of sodium hydrogen carbonate, and saturated solution of sodium chloride, dried on magnesium sulfate, and concentrated. The residue (198 mg) is purified by chromatography on silica gel (10 g) containing 10% water, and eluted with a mixture of benzene and ethyl acetate (1 : 1) to yield diphenylmethyl 7β-[α-(3-thienyl)-α-t-butoxycarbonylacetamido]-3-(1-methyltetrazol-5-yl)thiomethyl-1-oxadethia-3-cephem-4-carboxylate (56 mg) as colorless powder. mp. 85 - 90° C.
Yield: 39.7%.

IR: $\nu_{max}^{CHCl_3}$ 1798, 1720, 1685, 1630 cm$^{-1}$.

NMR: $\delta^{CDCl_3}$ 1.45s9H, 3.85s3H, 4.32s2H, 4.67m3H, 5.06d(4Hz)1H, 5.86dd(10;4Hz)1H, 7.00s1H, 7.1 – 7.65m14H.

Example II 11

To a solution of diphenylmethyl 7β-amino-3-(1-t-butoxycarboxylmethyltetrazol-5-yl)thiomethyl-1-oxadethia-3-cephem-4-carboxylate (102 mg) in a mixture of tetrahydrofuran (2 ml) and acetone (1 ml) are added monobenzhydryl α-phenylmalonate (186 mg) and N-ethoxycarbonyl-2-ethoxy-1,2-dihydroquinoline (88 mg) in two portions, and the mixture is stirred at room temperature for 3.5 hours. The reaction mixture is mixed with ethylacetate, washed with 2N-hydrochloric acid, water, 5% sodium hydrogencarbonate aqueous solution and water, dried on sodium sulfate, and concentrated under reduced pressure. The residue is chromatographed on silica gel (10 g) containing 10% water, eluted with a mixture of benzene and ethyl acetate (9 : 1), and concentrated to give diphenylmethyl 7β-(α-diphenylmethoxycarbonyl-α-phenylacetamido)-3-(1-t-butoxycarbonylmethyltetrazol-5-yl)thiomethyl-1-oxadethia-3-cephem-4-carboxylate (63 mg) as colorless foam. Yield: 39%.

IR: $\nu_{max}^{CHCl_3}$ 1800, 1750, 1725, 1680 cm$^{-1}$.

NMR: $\delta^{CDCl_3}$ 6.96s1H, 6.93s1H, 5.75dd(4;9Hz)1H, 5.03d(4Hz)1H, 4.90s2H, 4.73s1H/2, 4.71s1H/2, 4.60brs2H, 4.30s2H, 1.40s9H.

Example II-12

To a solution of diphenylmethyl 7β-amino-3-(1-t-butoxycarbonylmethyltetrazol-5-yl)thiomethyl-1-oxadethia-3-cephem-4-carboxylate (87 mg) in acetonitrile (2 ml) are added N-[α-t-butoxycarbonyl-α-(2-thienyl)acetoxy]succinimide (76 mg) and N-methylmorpholine (0.016 ml) in nitrogen atmosphere, and the mixture is stirred for 90 minutes. The reaction mixture is mixed with ethyl acetate, washed with dilute hydrochloric acid, water, 5% sodium hydrogencarbonate aqueous solution, and water, dried on sodium sulfate, and concentrated. The residue is chromatographed on silica gel (10 g) containing 10% water, and eluted with a mixture of benzene and ethyl acetate (9 : 1) to give diphenylmethyl 7β-[α-t-butoxycarbonyl-α-(2-thienyl)-acetamido]-3-(1-t-butoxycarbonylmethyltetrazol-5-yl)thiomethyl-1-oxadethia-3-cephem-4-carboxylate (96 mg) as colorless form. Yield: 80%.

IR: $\nu_{max}^{CHCl_3}$ 1802, 1750, 1722, 1690 cm$^{-1}$.

NMR: $\delta^{CDCl_3}$ 6.93s1H, 5.72dd(4;9Hz)1H, 5.06d(4Hz)1H, 4.83s2H, 4.75brs1H, 4.60brs2H, 4.30s2H, 1.45s18H.

EXAMPLE II-13

To a solution of diphenylmethyl 7β-amino-3-(2-methyl-1,3,4-thiadiazol-5-yl)thiomethyl-1-oxadethia-3-cephem-4-caboxylate (215 mg) in a mixture of tetrahydrofuran (4 ml) and acetone (2 ml) are added three lots of hemidiphenylmethyl α-phenylmalonate (131 mg × 3) and 1-ethoxycarbonyl-2-ethoxy-1,2-dihydroquinoline (107 mg × 3) at room temperature in 1.5 hours interval. After 2 hours, the reaction mixture is diluted with ethyl acetate, washed with water, diluted hydrochloric acid, water, aqueous sodium hydrogencarbonate, and water, dried on sodium sulfate, and concentrated. The residue is purified by chromatography on silica gel (30 g) containing 10% water, eluted with a mixture of benzene and ethyl acetate (4 : 1), and the eluate is triturated with a mixture of ether and n-pentane to give diphenylmethyl 7β-(α-phenyl-α-diphenylmethoxycarbonylacetamido)-3-(2-methyl-1,3,4-thiadiazol-5-yl) thiomethyl-1-oxadethia-3-cephem-4-carboxylate (170 mg) as colorless foam. Yield: 47.5%.

IR: $\nu_{max}^{CHCl_3}$ 3350, 1799, 1715, 1690sh cm$^{-1}$.

NMR: $\delta^{CDCl_3}$ 2.67s3H, 4.22 + 4.53ABq(14Hz)2H, 4.57s2H, 4.75s1H, 5.00d(4Hz)1H, 5.73dd(4;9.5Hz)1H, 6.92s1H, 6.97s1H.

EXAMPLE II-14

To a solution of α-diphenylmethoxycarbonyl-α-phenyl-acetic acid (103.9 mg) in methylene chloride (2 ml) cooled at 0° C are added triethylamine (0.042 ml) and oxalyl chloride (0.0256 ml). After stirring for 10 minutes at 0° C, the mixture is poured into a solution of diphenylmethyl 7β-amino-7α-methoxy-3-(1-methyltetrazol-5-yl) thiomethyl-1-oxadethia-3-cephem-4-carboxylate (101.7 mg) and pyridine (0.0594 ml) in methylene chloride (5 ml) at 0° C, stirred for 1 hour at 0° C, diluted with ethyl acetate, washed with dilute hydrochloric hydrochloric acid, water, aqueous sodium hydrogencarbonate, and water, dried on sodium sulfate, and concentrated under reduced pressure. The obtained residue is chromatographed on silica gel (20 g) containing 10% water, and eluted with a mixture of benzene and ethyl acetate (4 : 1) to give diphenylmethyl 7β-(α-diphenylmethoxycarbonyl-α-phenylacetamido)7α-methoxy-3-(1-methyltetrazol-5-yl)thiomethyl-1-oxadethia-3-cephem-4-carboxylate (121.2 mg) as colorless foam. Yield: 72.4%.

IR: $\nu_{max}^{CHCl_3}$ 3320, 1792, 1725, 1700 cm$^{-1}$.

NMR: $\delta^{CDCl_3}$ (3.40s + 3.42s)3H, 3.69s3H, 4.22s2H, 4.45s2H, 4.75s1H, 5.00s1H, 6.92s2H, 7.85s1H.

EXAMPLE II-15

A mixture of α-(indan-5-yl)oxycarbonyl-α-phenylacetic acid (148 mg) and thionyl chloride (0.25 ml) is heated at 70° C for 1 hour, and evaporated under reduced pressure. The residue is dissolved in benzene (2 ml) and evaporated again to dryness. The residue is dissolved in methylene chloride (2 ml), and poured into a solution of diphenylmethyl 7β-amino-7α-methoxy-3-(1-methyltetrazol-5-yl)thiomethyl-1-oxadethia-3-cephem-4-carboxylate (101.7 mg) and pyridine (0.016 ml) in methylene chloride (4 ml) at 0° C. After stirring for 30 minutes at 0° C, the mixture is diluted with ethyl acetate, washed with aqueous sodium hydrogencarbonate, water, diluted hydrochloric acid, and water, dried on sodium sulfate, and evaporated under reduced pressure. The residue is chromatographed on silica gel (20 g) containing 10% water to give diphenylmethyl 7β-[α-(indan-5-yl) oxycarbonyl-α-phenylacetamido]-7α-methoxy-3-(1-methyltetrazol-5-yl)thiomethyl-1-oxadethia-3-cephem-4-carboxylate (116.1 mg) as colorless foam. Yield: 73.8%.

IR: $\nu_{max}^{CHCl_3}$ 3390, 3320, 1780, 1727, 1700 cm$^{-1}$.

NMR: $\delta^{CDCl_3}$ 2.05quintet(7Hz)2H, 2.87t(7Hz)4H, 3.48s3H, 3.77s3H, 4.23s2H, 4.53s2H, 4.87s1H, 5.02s1H

EXAMPLE II-16

To a solution of α-diphenylmethoxycarbonyl-α-p-acetoxyphenylacetic acid (142 mg) in methylene chloride (2 ml) cooled at 0° C are added triethylamine (0.0416 ml) and oxalyl chloride (0.0256 ml). After stirring for 15 minutes at 0° C, the mixture is mixed gradually with a solution of diphenylmethyl 7β-amino-7α-methoxy-3-(1-methyltetrazol-5-yl)thiomethyl-1-oxadethia-3-cephem-4-carboxylate (101.7 mg) and pyridine (0.024 ml) in methylene chloride (4 ml) at 0° C, stirred for 15 minutes, diluted with ethyl acetate, washed with aqueous sodium hydrogencarbonate, water, diluted hydrochloric acid, and water, dried on sodium sulfate, and concentrated under reduced pressure. The obtained residue is chromatographed on silica gel (20 g) containing 10% water to give diphenylmethyl 7β-(60-diphenylmethoxycarbonyl-α-p-acetoxyphenylacetamido)-7α-methoxy-3-(1-methyltetrazol-5-yl)-thiomethyl-1-oxadethia-3-cephem-4-carboxylate (133.4 mg) as colorless foam from fractions eluted with a mixture of benzene and ethyl acetate (2 : 1).

Yield: 74.5%.

IR: $\nu_{max}^{CHCl_3}$ 3325, 1792, 1730, 1700sh cm$^{-1}$.

NMR: $\delta^{CDCl_3}$ 2.40s3H, 3.40s3H, 3.67s3H, 4.17s2H, 4.42s2H, 4.73s1H, 4.98s1H.

EXAMPLE II-17

To a solution of α-diphenylmethoxycarbonyl-α-p-hydroxyphenylacetic acid (254 mg) in methylene chloride (3 ml) are added triethylamine (0.083 ml) and oxalyl chloride (0.051 ml) at 0° C. After stirring for 15 minutes, the mixture is added to a solution of diphenylmethyl 7β-amino-7α-methoxy-3-(1-methyltetrazol-5yl)-thiomethyl-1-oxadethia-3-cephem-4-carboxylate (101.7 mg) and pyridine (0.048 ml) in methylene chloride (4 ml) at 0° C. After stirring for 30 minutes at 0° C, the mixture is diluted with ethyl acetate, washed with aqueous sodium hydrogencarbonate, water, hydrochloric acid, and water, dried on sodium sulfate, and evaporated under reduced pressure. The obtained residue is chromatographed on silica gel (20 g) containing 10% water and eluted with a mixture of benzene and ethyl acetate (2 : 1) to give diphenylmethyl 7β-(α-diphenylmethoxycarbonyl-α-p-hydroxyphenylacetamido)-7α-methoxy-3-(1-methyltetrazol-5-yl)thiomethyl-1-oxadethia-3-cephem-4-carboxylate (86.4 mg) as colorless foam. Yield: 49.6%.

IR: $\nu_{max}^{CHCl_3}$ 3585, 3315, 1790, 1722, 1700sh cm$^{-1}$.

NMR: $\delta^{CDCl_3}$ (3.45s + 3.48s)3H, (3.72s + 3.75s)3H, 4.18s2H, 4.45s2H, (4.67s + 4.70s)1H, 5.02s1H.

EXAMPLE II-18

To a suspension of α-(5-indanyl)oxycarbonyl-α-p-hydroxyphenylacetic acid (370 mg) in methylene chloride (4 ml) are added triethylamine (139 μl) and oxalyl chloride (85 μl) at 0° C in nitrogen to give clear solution. After stirring for 20 minutes at 0° C, the mixture is added to a solution of diphenylmethyl 7β-amino-7α-methoxy-3-(1-methyltetrazol-5-yl)-thiomethyl-1-oxadethia-3-cephem-4-carboxylate (203 mg) in methylene chloride (5 ml) and pyridine (80 μl), and the mixture is stirred for 10 minutes. The reaction mixture is diluted with ethyl acetate, washed with 2N-hydrochloric acid, water, 5% sodium hydrogencarbonate aqueous solution, and water, dried over sodium sulfate, and concentrated under reduced pressure to give pale yellow foam, which is chromatographed on silica gel (50 g) containing 10% water, and eluted with a mixture of benzene and acetic acid (1 : 1) to give diphenylmethyl 7β-[α-p-hydroxyphenyl-α-(5-indanyl)-oxycarbonylacetamido]-7α-methoxy-3-(1-methyltetrazol-5-yl)-thiomethyl-1-oxadethia-3-cephem-4-carboxylate as crystalline residue (230 mg); Yield: 71.6% which is recrystallized from a mixture of chloroform and ether to give pure crystals melting at 114 - 116° C.

UV: $\nu_{max}^{CH_3OH}$ 272 ($\epsilon$ = 9500), 284 ($\epsilon$ = 9260) nm.

NMR: $\delta^{CD_3COCD_3}$ 2.1m2H, 2.87t(7Hz)4H, 3.43s3H, 3.91s3H, 4.31s2H, 4.65s2H, 5.07s1H, 6.92brs3H.

IR: $\nu_{max}^{CHCl_3}$ 3590, 3335, 1789, 1736, 1722, 1700, 1601 cm$^{-1}$.

EXAMPLE II-19

To a solution of α-t-butoxycarbonyl-α-(3-thienyl)acetic acid (97 mg) in methylene chloride (1 ml) are added triethylamine (0.042 ml) and oxalyl chloride (0.026 ml) at 0° C in nitrogen atmosphere. After stirring for 30 minutes at 0° C, the mixture is poured into a solution of diphenylmethyl 7β-amino-7α-methoxy-3-(1-methyltetrazol-5-yl)thiomethyl-1-oxadethia-3-cephem-4-carboxylate (101 mg) and pyridine (0.024 ml) in methylene chloride (3 ml) at 0° C in nitrogen atmosphere. After stirring at 0° C for 90 minutes, the mixture is diluted with methylene chloride, washed with 5% sodium hydrogencarbonate in water, water, 2N-hydrochloric acid, and water, dried on sodium sulfate, concentrated under reduced pressure, chromatographed on silica gel (5 g) containing 10% water, and eluted with a mixture of benzene and ethyl acetate (2 : 1) to give diphenylmethyl 7β-[α-t-butoxycarbonyl-α-(3-thienyl)acetamido]-7α-methoxy-3-(1-methyltetrazol-5-yl)thiomethyl-1-oxadethia-3-cephem-4-carboxylate (144 mg) as colorless foam. Yield: quantitative.

IR: $\nu_{max}^{CHCl_3}$ 1795, 1720, ca. 1700 cm$^{-1}$.

NMR: $\delta^{CDCl_3}$ 6.96s1H, (5.07s + 5.05s)1H, 4.60brs3H, 4.30brs2H, 3.83s3H, (3.53s + 3.50s)3H, 1.41s9H.

EXAMPLE II-20

To a solution of 3-thienylmalonic acid indanyl ester (120 mg) in methylene chloride (1.5 ml) are added triethylamine (42 μl) and oxalyl chloride (26 μl) under ice cooling. After stirring for 15 minutes, the mixture is added to a solution of diphenylmethyl 7β-amino-7α-methoxy-3-(1-methyltetrazol-5-yl)-thiomethyl-1-oxadethia-3-cephem-4-carboxylate (116 mg) in methylene chloride (3 ml) and pyridine (24 μl), and the mixture is stirred at 0° C for 1 hour. The reaction mixture is poured into ethyl acetate, washed with 2N-hydrochloric acid, water, 5% sodium hydrogencarbonate aqueous solution, and water, dried over magnesium sulfate, and concentrated. The residue is chromatographed on silica gel (10 g) containing 10% water, and eluted with a mixture of benzene and ethyl acetate (10 : 1) to give diphenylmethyl 7β-[α-(3-thienyl)-α-(indan-5-yl)oxycarbonylacetamido]-7α-methoxy-3-(1-methyltetrazol-5yl) thiomethyl-1-oxadethia-3-cephem-4-carboxylate (140 mg). Yield: 78%.

IR: $\nu_{max}^{CHCl_3}$ 3400, 3327, 1789, 1736, 1712 cm$^{-1}$.

NMR: $\delta^{CDCl_3}$ 2.07m2H, 2.87br-t(7Hz)4H, 3.50s3H, 3.77s3H, 4.24s2H, 4.56s2H, 4.97s1H, (5.02s + 5.04 s)1H, 6.88brs3H. $[\alpha]_D^{22.5}$ − 68.2 ± 1.1° (c = 1.023, CHCl$_3$).

EXAMPLE II-21

To a solution of 3-thienylmalonic acid monobenzhydryl ester (710 mg) in methylene chloride (5 ml) are added triethylamine (210 μl) and oxalyl chloride (130 μl) under ice cooling. After stirring for 15 minutes at the same temperature, the mixture is added to a solution of diphenylmethyl 7β-amino-7α-methoxy-3-(1-methyltetrazol-5-yl)thiomethyl-1-oxadethia-3-cephem-4-carboxylate (510 mg) in methylene chloride (15 ml) and pyridine (120 μl) under ice cooling. After stirring for 30 minutes, the mixture is poured into ethyl acetate, washed with 2N-hydrochloric acid, water, 5% sodium hydrogencarbonate and water, dried on magnesium sulfate, and concentrated. The residue is chromatographed on silica gel (100 g) containing 10% water, and eluted with a mixture of benzene and ethyl acetate (10:1 - 4:1) to give diphenylmethyl 7β-[α-(3-thienyl)-α-diphenylmethoxycarbonylacetamido]-7α-methoxy-3-(1-methyltetrazol-5-yl)thiomethyl-1-oxadethia-3-cephem-4-carboxylate as colorless foam (834 mg).

IR: $\nu_{max}^{CHCl_3}$ 1790, 1728, 1710sh cm$^{-1}$.

NMR: $\delta^{CDCl_3}$ 3.30s3H, 3.60s3H, 4.09s2H, 4.37s2H, 4.79s1H, 4.90s1H, 6.87s2H.

EXAMPLE II-22 (phenyl ester)

To a suspension of 3-thienylmalonic acid monophenyl ester (105 mg) in methylene chloride (1.5 ml) are added triethylamine (42 μl) and oxalyl chloride (26 μl) under ice cooling.

After stirring for 15 minutes, the mixture is added to a solution of diphenylmethyl 7β-amino-7α-methoxy-3-(1-methyltetrazol-5-yl)thiomethyl-1-oxadethia-3-cephem-4-carboxylate (116 mg) in methylene chloride (3 ml) and pyridine (24 μl) at 0° C, and the mixture is stirred at 0° C for 1 hour. The reaction mixture is poured into ethyl acetate, washed with 2N-hydrochloric acid, water, 5% sodium hydrogencarbonate aqueous solution, and water, dried over magnesium sulfate, and concentrated. The residue is chromatographed on silica gel (10 g) containing 10% water, and eluted with a mixture of benzene and ethyl acetate (8 : 1) to give diphenylmethyl 7β-[α-(3-thienyl)-α-phenoxycarbonylacetamido]-7α-methoxy-3-(1-methyltetrazol-5-yl)thiomethyl-1-oxadethia-3-cephem-4-carboxylate as colorless foam (125 mg). Yield: 76%.

IR: $\nu_{max}^{CHCl_3}$ 3406, 3341, 1789, 1740, 1711 cm$^{-1}$.

NMR: $\delta^{CDCl_3}$ 3.49s3H, 3.78s3H, 4.24s2H, 4.55s2H, 4.97s1H, 5.03s1H, 6.88s1H.

$[\alpha]_D^{22.5}$ −74.8 ± 1.1° (c = 1.005 CHCl$_3$).

EXAMPLE II-23

To a solution of 3-thienylacetic acid mono-3,4-dimethyl-phenyl ester (120 mg.) in methylene chloride (1.5 ml) are added triethylamine (42 μl) and oxalyl chloride (26 μl) under ice cooling. After stirring for 15 minutes, the mixture is added to a solution of diphenylmethyl 7β-amino-7α-methoxy-3-(1-methyltetrazol-5-yl)-thiomethyl-1-oxadethia-3-cephem-4-carboxylate (116 mg) in methylene chloride (3 ml) and pyridine (24 μl), and the mixture is stirred at 0° C for 1 hour. The reaction mixture is poured into ethyl acetate, washed with 2N-hydrochloric acid, water, 5% sodium hydrogencarbonate aqueous solution, and water, dried over magnesium sulfate, and concentrated. The residue is chromatographed over silica gel (10 g) containing 10 % water, and eluted with a mixture of benzene and ethyl acetate (10 : 1) to give diphenylmethyl 7β-[α-(3-thienyl)-α-(3,4-dimethylphenyl)oxycarbonylacetamido]-7α-methoxy-3-(1-methyltetrazol-5-yl)thiomethyl-1-oxadethia-3-cephem-4-carboxylate (128 mg). Yield: 72%.

IR: $\nu_{max}^{CHCl_3}$ 3405, 3340, 1790, 1737, 1712 cm$^{-1}$.

NMR: $\delta^{CDCl_3}$ 2.22s6H, 3.50s3H, 3.76s3H, 4.24s2H, 4.56s2H, 4.95s1H, (5.00s + 5.02s)1H, 6.86s2H, 6.90s1H. $[\alpha]_D^{22.5}$ −68.1 ± 1.1° (c = 1.002, CHCl$_3$).

EXAMPLE II-24

To a solution of α-diphenylmethoxycarbonyl-α-(2-thienyl)-acetic acid (176 mg) in methylene chloride (1 ml) are added triethylamine (0.055 ml) and oxalyl chloride (0.034 ml) at 0° C, under nitrogen. After stirring for 15 minutes at 0° C, the mixture is added to a solution of diphenylmethyl 7β-amino-7α-methoxy-3-(1-methyltetrazol-5-yl)thiomethyl-1-oxadethia-3-cephem-4-carboxylate (101 mg) and pyridine in methylene chloride (3 ml) at 0° C. The mixture is stirred for 30 minutes, diluted with ethyl acetate, washed with 5% sodium hydrogencarbonate aqueous solution, water, 2N-hydrochloric acid, and water, dried on sodium sulfate, and concentrated under reduced pressure. The obtained residue is chromatographed on silica gel (10 g) containing 10 % water, and eluted with a mixture of benzene and ethyl acetate (4 : 1) to give diphenylmethyl 7β-[α-diphenylmethoxycarbonyl-α-(2-thienyl)acetamido]-7α-methoxy-3-(1-methyltetrazol-5-yl)-thiomethyl-1-oxadethia-3-cephem-4-carboxylate (140 mg) as colorless foam. Yield: 85 %.

IR: $\nu_{max}^{CHCl_3}$ 1785, 1720, ca. 1700 cm$^{-1}$.
NMR: $\delta^{CDCl_3}$ 6.93s2H, 5.00s2H, 4.50brs2H, 4.15brs2H, 3.80s3H, 3.40brs3H.

EXAMPLE II-25

To a solution of α-(p-benzyloxyphenyl)malonic acid mono-benzyl ester (376 mg) in methylene chloride (4 ml) are added triethylamine (105 μl) and oxalyl chloride (65 μl) under ice cooling. After stirring for 15 minutes under ice-cooling, the mixture is added to a solution of diphenylmethyl 7β-amino-7α-methoxy-3-(1-methyltetrazol-5-yl)thiomethyl-1-oxadethia-3-cephem-4-carboxylate (254 mg) and pyridine (60 μl) in methylene chloride (7 ml) under ice cooling. After stirring for 30 minutes at the same temperature, the mixture is poured into ethyl acetate, washed with 2N-hydrochloric acid, water, 5% sodium hydrogencarbonate aqueous solution, and water, dried over magnesium sulfate, and evaporated. The residue is chromatographed on silica gel (20 g) containing 10water, and eluted with a mixture of benzene and ethyl acetate (10 : 1) to give diphenylmethyl 7β-[α-(p-benzyloxyphenyl)-α-benzyloxycarbonylacetamido]-7α-methoxy-3-(1-methyltetrazol-5-yl)thiomethyl-1-oxadethia-3-cephem-4-carboxylate as colorless foam (390 mg).

NMR: $\delta^{CDCl_3}$ 3.38s3H, 3.62s3H, 4.13s2H, 4.45s2H, 4.56s1H, 4.96s3H, 5.09s2H, 6.82d(9Hz)2H, 6.84s1H.
IR: $\nu_{max}^{CHCl_3}$ 3411, 3326, 1789, 1722, 1700sh cm$^{-1}$.
$[\alpha]_D^{23}$ −72.0 ± 2° (c = 0.553, CHCl$_3$).

EXAMPLE II-26

To a solution of α-diphenylmethoxycarbonyl-p-(p-methoxybenzyl)oxyphenylacetic acid (193 mg) in methylene chloride (2 ml) are added triethylamine (0.0416 ml) and oxalyl chloride (0.0256 ml) at 0° C, and the mixture is stirred for 30 minutes. The resulting solution is added to a solution of diphenylmethyl 7β-amino-7α-methoxy-3-(1-methyltetrazol-5-yl)thiomethyl-1-oxadethia-3-cephem-4-carboxylate (101.7 mg) and pyridine (0.024 ml) in methylene chloride (4 ml) at 0° C. After stirring for 30 minutes at 0° C, the mixture is diluted with ethyl acetate, washed with water, dried on sodium sulfate, and concentrated. The residue is chromatographed on silica gel (20 g) containing 10% water, and eluted with a mixture of benzene and ethyl acetate (4 : 1) to give diphenylmethyl 7β-[α-p-(p-methoxybenzyl)oxyphenyl-α-diphenylmethoxycarbonylacetamido]-7α-methoxy-3-(1-methyltetrazol-5-yl)thiomethyl-1-oxadethia-3-cephem-4-carboxylate (190.7 mg) as colorless foam. Yield: 98%.

IR: $\nu_{max}^{CHCl_3}$ 3420, 3325, 1792, 1730, 1700 sh cm$^{-1}$.
NMR: $\delta^{CDCl_3}$ (3.38s + 3.40s)3H, 3.70s3H, 3.77s3H, 4.20s2H, 4.47s2H, 4.68s1H, 4.95s2H, 5.00s1H.

EXAMPLE II-27

In a procedure similar to that of Example II-26, diphenylmethyl 7β-amino-7α-methoxy-3-(1-methyltetrazol-5-yl)thiomethyl-1-oxadethia-3-cephem-4-carboxylate (800 mg) is treated with α-p-(p-methoxybenzyl)oxyphenyl-α-p-methoxybenzyloxycarbonylacetyl chloride prepared from the corresponding free acid (1370 mg) and oxalyl chloride in the presence of pyridine (190 mg) and triethylamine (0.33 ml) in methylene chloride (42 ml) to give diphenylmethyl 7β-[α-p-(p-methoxybenzyl)oxyphenyl-α-p-methoxy-benzyloxycarbonylacetamido]-7α-methoxy-3-(1-methyltetrazol-5-yl)thiomethyl-1-oxadethia-3-cephem-4-carboxylate (1.45 g).

Yield: nearly quantitative.
IR: $\nu_{max}^{CHCl_3}$ 1792, 1725, 1700sh cm$^{-1}$.
NMR: $\delta^{CDCl_3}$ 3.45s3H/2, 3.48s3H/2, 3.78s6H, 3.82s3H, 4.27brs2H, 4.57brs3H, 4.98s2H, 5.03s1H 5.13s2H.

EXAMPLE II-28

To a stirred suspension of p-(p-methoxybenzyloxy)-phenylmalonic acid (125 mg) in methylene chloride (3 ml) are added triethylamine (55 μl) and oxalyl chloride (26 μl) at −15° C, and the suspension is stirred for 40 minutes at 0° C. The mixture is added to a solution of diphenylmethyl 7β-amino-7α-methoxy-3-(1-methyltetrazol-5-yl)thiomethyl-1-oxadethia-3-cephem-4-carboxylate (100 mg) in methylene chloride (3 ml) and pyridine (63 μl), and the mixture is stirred for 30 minutes at 0° C. The reaction mixture is diluted with ethyl acetate, washed with aqueous 2N-hydrochloric acid and water, dried over sodium sulfate, and concentrated to give crude product (212 mg), which is chromatographed on silica gel (20 g) and eluted with a mixture of ethyl acetate and acetic acid (99:1) to give diphenylmethyl 7β-[α-p-(p-methoxybenzyloxy)phenyl-α-carboxyacetamido]-7α-methoxy-3-(1-methyltetrazol-5-yl)thiomethyl-1-oxadethia-3-cephem-4-carboxylate as foam (71 mg). Yield: 45%.

IR: $\nu_{max}^{CHCl_3}$ 3385, 3300-2400br, 1790, 1762, 1714, 1612 cm$^{-1}$.
NMR: $\delta^{CDCl_3}$ 3.43s3H/2, 3.46s3H/2, 3.74s3H, 3.78s6H, 4.22brs2H, 4.56brs3H, 4.96s2H, 5.05s1H.

The product obtained above (40 mg) gives 7β-(α-p-hydroxyphenyl-α-carboxyacetamido)-7α-methoxy-3-(1-methyltetrazol-5-yl)thiomethyl-1-oxadethia-3-cephem-4-carboxylic acid by the action of trifluoroacetic acid (0.2 ml) and anisole (0.4 ml) at 0° C for 20 minutes.

III. Deprotection

EXAMPLE III-1

To a solution of diphenylmethyl 7β-(α-phenyl-α-diphenylmethoxycarbonylacetamido)-3-(1-methyltetrazol-5-yl)thiomethyl-1-oxadethia-3-cephem-4-carboxylate (120 mg) in methylene chloride (3 ml) are added anisole (0.3 ml) and trifluoroacetic acid (0.3 ml) in nitrogen atmosphere at 0° C, and the mixture is stirred for 1.5 hours. The reaction mixture is concentrated under reduced pressure. The residue is purified by chromatography on silica gel (10 g) containing 10% water, and eluted with a mixture of ethyl acetate and acetic acid (9:1) to give 7β-(α-phenyl-α-carboxyacetamido)-3-(1-methyltetrazol-5-yl)thiomethyl-1-oxadethia-3-cephem-4-carboxylic acid (57 mg) as powder. mp. 157° - 159° C (decomposition). Yield: 81%.

IR: $\nu_{max}^{Nujol}$ 1778, 1670, 1606 cm$^{-1}$.

IR: $\nu_{max}^{KBr}$ 3420, 2520br, 1775, 1674, 1606, 1528.5, 1376 cm$^{-1}$.

UV: $\lambda_{max}^{1\% NaHCO_3}$ 265.5 nm ($\epsilon$=9442).

NMR: $\delta^{1\% NaHCO_3 \ in \ D_2O}$ 4.02s3H, 4.05 + 4.32ABq(13.5Hz)2H, 4.55brs2H, 5.16d(4Hz)1H/2, 5.21d(4Hz)1H/2, 5.48d(4Hz)1H, 7.37s5H, 5.08brs1H (the last peak gradually diminished).

$[\alpha]_D^{23}$ − 90.3 ± 4.2° (c = 0.310, 1% NaHCO$_3$).

CD: $\lambda(\theta)$ (0.155% NaHCO$_3$) 305(0), 285(− 2500), 276.5(0), 258(+ 11700), 249.5(0), 232(− 59100), 210(− 3500).

EXAMPLE III-2

To a solution of diphenylmethyl 7β-[α-(5-indanyl)oxycarbonyl-α-phenylacetamido]-3-(1-methyltetrazol-5-yl)thiomethyl-1-oxadethia-3-cephem-4-carboxylate (144 mg) in methylene chloride (3 ml) are added anisole (0.2 ml) and trifluoroacetic acid (0.4 ml) under ice cooling, and the mixture is stirred for 2 hours. The reaction mixture is diluted with ethyl acetate, washed with water and aqueous sodium hydrogencarbonate, dried, and evaporated. To the residue is triturated with ether, and the resulting powder is collected by filtration to give sodium 7β-[α-(5-indanyl)oxycarbonyl-α-phenylacetamido]-3-(1-methyltetrazol-5-yl)thiomethyl-thiomethyl-1-oxadethia-3-cephem-4-carboxylate (60 mg).

IR: $\nu_{max}^{Nujol}$ 1760, 1690sh, 1670 cm$^{-1}$.

Example III-3

To a solution of diphenylmethyl 7β-α-carboxy-α-phenylacetamido)-3-(1-methyltetrazol-5-yl)thiomethyl-1-oxadethia-3-cephem-4-carboxylate (576 mg) in methylene chloride (10 ml) are added anisole (1 ml) and trifluoroacetic acid (1 ml) in nitrogen atmosphere under ice cooling, and the mixture is stirred for 70 minutes. The reaction mixture is concentrated under reduced pressure to give 7β-(α-phenyl-α-carboxyacetamido)-3-(1-methyltetrazol-5-yl)thiomethyl-1-oxadethia-3-cephem-4-carboxylic acid.

Yield: nearly quantitative. Crude product.

IR: $\nu_{max}^{Nujol}$ 1778, 1670, 1604 cm$^{-1}$.

Example III-4

To a solution of 7β-(α-diphenylmethoxycarbonyl-α-phenylacetamido)-3-(1-methyltetrazol-5-yl)thiomethyl-1-oxadethia-3-cephem-4-carboxylic acid (72 mg) in methylene chloride (2 ml) are added anisole (0.2 ml) and trifluoroacetic acid (0.2 ml) at 0° C. After 50 minutes under ice-cooling, the reaction mixture is concentrated under reduced pressure. The residue is purified by chromatography on silica gel (5 g) containing 10% water, and eluted with a mixture of acetic acid and ethyl acetate (1 : 9) to give 7β-(α-carboxy-α-phenylacetamido)-3-(1-methyltetrazol-5-yl)thiomethyl-1-oxadethia-3-cephem-4-carboxylic acid (41 mg). mp. 165° - 170° C (decomposition).

Yield: 75%.

IR: $\nu_{max}^{Nujol}$ 1778, 1670, 1605 cm$^{-1}$.

Example III-5

A solution of diphenylmethyl 7β-(α-p-nitrobenzyloxycarbonyl-α-phenylacetamido)-3-(1-methyltetrazol-5-yl)thiomethyl-1-oxadethia-3-cephem-4-carboxylate (715 mg) in a mixture of methanol (40 ml) and tetrahydrofuran (40 ml) is shaken in the presence of pre-reduced 5% palladium on carbon (700 mg) and 10% hydrochloric acid (2 ml) under hydrogen at 1 atm. and at room temperature for 70 minutes. The reaction mixture is filtered to remove the catalyst, diluted with water (120 ml) containing 10% hydrochloric acid (2 ml), concentrated to remove the organic solvent, and extracted with ethyl acetate. The extract is washed with water, dried on magnesium sulfate, and evaporated under reduced pressure to give diphenylmethyl 7β-(α-carboxy-α-phenylacetamido)-3-(1-methyltetrazol-5-yl)thiomethyl-1-oxadethia-3-cephem-4-carboxylate (576 mg). Yield: 97.6% (crude).

Example III-6

A mixture of diphenylmethyl 7β-(α-p-hydroxyphenyl-α-t-butoxycarbonylacetamido)-3-(1-methyltetrazol-5-yl)thiomethyl-1-oxadethia-3-cephem-4-carboxylate (74 mg), thiophenol (0.075 ml), and trifluoroacetic acid (0.75 ml) is stirred for 1.5 hours under ice-cooling. The reaction mixture is evaporated under reduced pressure. The residue is purified by chromatography on silica gel containing 10% water, and eluted with a mixture of acetic acid and ethyl acetate (1 : 9). The eluate is triturated with a mixture of ether and pentane to give 7β-(α-p-hydroxyphenyl-α-carboxyacetamido)-3-(1-methyltetrazol-5-yl)thiomethyl-1-oxadethia-3-cephem-4-carboxylic acid (30 mg). Yield: 58.9%.

mp. 130° - 142° (decomposition).

IR: $\nu_{max}^{KBr}$ 3400, 1787, 1720 cm$^{-1}$.

UV: $\lambda_{max}^{CH_3OH}$ 273 nm ($\epsilon$=7850).

Example III-7

To a solution of diphenylmethyl 7β-(α-p-hydroxyphenyl-α-diphenylmethoxycarbonylacetamido)-3-(1-methyltetrazol-5-yl)thiomethyl-1-oxadethia-3-cephem-4-carboxylate (137 mg) in methylene chloride (3 ml) are added anisole (0.3 ml) and trifluoroacetic acid (0.3 ml) at 0° C under nitrogen. After stirring for 1 hour at 0° C, the mixture is concentrated under reduced pressure, triturated with ether, and washed with ether to give 7β-(α-p-hydroxyphenyl-α-carboxyacetamido)-3-(1-methyltetrazol-5-yl)thiomethyl-1-oxadethia-3-cephem-4-carboxylic acid as colorless powder (81 mg) decomposing at 130° - 142° C.

Yield: 59.6%.

IR: $\nu_{max}^{KBr}$ 3400, 1787, 1720 cm$^{-1}$.

UV: $\lambda_{max}^{CH_3OH}$ 273 nm ($\epsilon$=7850).

Example III-8

To a solution of diphenylmethyl 7β-[α-(2-thienyl)-α-t-butoxycarbonylacetamido]-3-(1-methyltetrazol-5-yl)thiomethyl-1-oxadethia-3-cephem-4-carboxylate (49 mg) in methylene chloride (1 ml) are added anisole (0.4 ml) and trifluoroacetic acid (1 ml) at 0° C, and the mixture is stirred under ice-cooling for 4 hours and at room temperature for 40 minutes. The reaction mixture is concentrated under reduced pressure. The residue is purified by chromatography on silica gel (5 g) containing 10% water, and eluted with a mixture of ethyl acetate and acetic acid (9:1). The eluate is triturated in ether to give 7β[α-(2-thienyl)-α-carboxyacetamido]-3-

(1-methyltetrazol-5-yl)thiomethyl-1-oxadethia-3-cephem-4-carboxylic acid (23 mg) as amorphous powder. mp. 156° - 160° C (decomposition with foaming). Yield: 33.5%.

IR: $\nu_{max}^{KBr}$ 3390, 1765, 1670, 1608, 1520 cm$^{-1}$.
$[\alpha]_D^{23}$ − 62.0 ± 3.7° (c=0.279, 1% NaHCO$_3$).
CD: $\lambda(\theta)$ (0.279, 1% NaHCO$_3$) 300(0), 282(− 2600), 276(0), 259(+ 11100), 249(0), 231.5(− 47400), 210(− 9700).

Example III-9

A mixture of diphenylmethyl 7β-[α-(3-thienyl)-α-t-butoxycarbonylacetamido]-3-(1-methyltetrazol-5-yl)thiomethyl-1-oxadethia-3-cephem-4-carboxylate (56 mg), anisole (0.35 ml), and trifluoroacetic acid (0.35 ml) is stirred at 0° C for 2 hours. The reaction mixture is evaporated under reduced pressure. The residue is purified by chromatography on silica gel (5 g) containing 10% water, eluted with a mixture of ethyl acetate and acetic acid (9:1) and triturated in a mixture of n-pentane and ether (2:1) to give 7β-[α-(3-thienyl)-α-carboxyacetamido]-3-(1-methyltetrazol-5-yl)thiomethyl-1-oxadethia-3-cephem-4-carboxylic acid (37mg) as colorless powder. mp. 155° - 160° C.
Yield: 96.8%.
IR: $\nu_{max}^{Nujol}$ 3400, 1770, 1692, 1610 cm$^{-1}$.

Example III-10

To a solution of diphenylmethyl 7β-(α-diphenylmethoxycarbonyl-α-phenylacetamido)-3-(1-t-butoxycarbonylmethyltetrazol-5-yl)thiomethyl-1-oxadethia-3-cephem-4-carboxylate (60 mg) in anisole (0.5 ml) is added trifluoroacetic acid (1 ml) under ice-cooling in nitrogen, and the mixture is kept at 0° C overnight. The reaction mixture is concentrated under reduced pressure, and the residue is triturated with ethyl acetate to give crude 7β-(α-carboxy-α-phenylacetamido)-3-(1-carboxymethyltetrazol-5-yl)-thiomethyl-1-oxadethia-3-cephem-4-carboxylic acid (22 mg) as powder. Yield: 64%.
IR: $\nu_{max}^{KBr}$ 1775, 1725 cm$^{-1}$.

Example III-11

To a solution of diphenylmethyl 7β-[α-t-butoxycarbonyl-α-(2-thienyl)acetamido]-3-(1-t-butoxycarbonylmethyltetrazol-5-yl)thiomethyl-1-oxadethia-3-cephem-4-carboxylate (96 mg) in anisole (0.5 ml) is added trifluoroacetic acid (1.5 ml) in nitrogen atmosphere under ice-cooling, and the mixture is allowed to stand overnight under ice-cooling. The reaction mixture is concentrated under reduced pressure. The residue is triturated with a mixture of ether and ethyl acetate to give crude 7β-[α-(2-thienyl)-α-carboxyacetamido]-3-(1-carboxymethyltetrazol-5-yl)thiomethyl-1-oxadethia-3-cephem-4-carboxylic acid (30 mg). mp. decomposition from 160° C. Yield: 48%.
IR: $\nu_{max}^{KBr}$ 1780, 1725 cm$^{-1}$.

Example III-12

To a solution of diphenylmethyl 7β-(α-phenyl-α-diphenylmethoxycarbonylacetamido)-3-(2-methyl-1,3,4-thiadiazol-5-yl)thiomethyl-1-oxadethia-3-cephem-4-carboxylate (170 mg) in methylene chloride (3 ml) are added anisole (0.2 ml) and trifluoroacetic acid (0.4 ml) at 0° C, and the mixture is stirred at 0° C for 1.5 hours. The reaction mixture is concentrated under reduced pressure. The residue is purified on silica gel (10 g) containing 10% water, eluted with a mixture of ethyl acetate and acetic acid (9:1), and triturated with a mixture of ethyl acetate and ether to give 7β-(α-phenyl-α-carboxyacetamido)-3-(2-methyl-1,3,4-thiadiazol-5-yl)thiomethyl-1-oxadethia-3-cephem-4-carboxylic acid (45.8 mg) as colorless powder. Yield: 45.1%. mp. 130° - 132° C.
IR: $\nu_{max}^{KBr}$ 3410, 1772, 1600 cm$^{-1}$.

Example III-13

To a solution of diphenylmethyl 7β-(α-diphenylmethoxycarbonyl-α-phenylacetamido)-7α-methoxy-3-(1-methyltetrazol-5-yl)thiomethyl-1-oxadethia-3-cephem-4-carboxylate (121.2 mg) in methylene chloride (2 ml) are added anisole (0.2 ml) and trifluoroacetic acid (0.4 ml) at 0° C. After stirring at 0° C for 1 hour, the reaction mixture is concentrated under reduced pressure and triturated with ether to give 7β-(α-carboxy-α-phenylacetamido)-7α-methoxy-3-(1-methyltetrazol-5-yl)thiomethyl-1-oxadethia-3-cephem-4-carboxylic acid (46.5 mg) as colorless powder.
Yield: 59.8%. mp. 110° - 116° C.
UV: $\lambda_{max}^{CH_3OH}$ 275.5 nm ($\epsilon$=9400). $[\alpha]_D^{25}$ − 19.4 ± 2.8° (c=0.211, CH$_3$OH).
IR: $\nu_{max}^{KBr}$ 1780, 1717, 1631 cm$^{-1}$.
NMR: $\delta^{D_2O}$ + NaHCO$_3$ (3.46s + 3.53s)3H, (3.99s + 4.02s)3H, 4.0 − 4.2m2H, 4.48s2H, 4.53s1H, 5.13s1H, 7.38s5H.

Example III-14

To a solution of diphenylmethyl 7β-(α-diphenylmethoxycarbonyl-α-p-acetoxyphenylacetamido)-7α-methoxy-3-(1-methyltetrazol-5-yl)thiomethyl-1-oxadethia-3-cephem-4-carboxylate (133.4 mg) in methylene chloride (2 ml) are added anisole (0.2 ml) and trifluoroacetic acid (0.4 ml) at 0° C. The mixture is stirred for 45 minutes, evaporated, and triturated with a mixture of ether and pentane, and ether to give 7β-(α-carboxy-α-p-acetoxyphenylacetamido)-7α-methoxy-3-(1-methyltetrazol-5-yl)thiomethyl-1-oxadethia-3-cephem-4-carboxylic acid (77 mg) as colorless foam. mp. 110° - 115° C. Yield: 91.9%
UV: $\lambda_{max}^{CH_3OH}$ 275 nm ($\epsilon$=9300).
$[\alpha]_D^{25}$ − 27.5 ± 2.6° (c =0.258, CH$_3$OH).
IR: $\nu_{max}^{KBr}$ 1782, 1728, 1635 cm$^{-1}$.
NMR: $\delta^{D_2O}$ + $^{NaHCO_3}$ 2.33s3H, (3.47s + 3.53s)3H, (3.99s + 4.02s)3H, ca. 4.13brs2H, 4.46brs2H, 5.13s1H, 7.12 + 7.47ABq(8Hz)4H.

Example III-15

To a solution of diphenylmethyl 7β-(α-diphenylmethoxycarbonyl-α-p-hydroxyphenylacetamido)-7α-methoxy-3-(1-methyltetrazol-5-yl)thiomethyl-1-oxadethia-3-cephem-4-carboxylate (84.6 mg) in methylene chloride (2 ml) are added anisole (0.1 ml) and trifluoroacetic acid (0.3 ml) at 0° C. After stirring for 45 minutes at 0° C, the mixture is evaporated under reduced pressure and triturated with a mixture of ether and n-pentane, and ether to yield 7β-(α-carboxy-α-p-hydroxyphenylacetamido)-7α-methoxy-3-(1-methyltetrazol-5-yl) thiomethyl-1-oxadethia-3-cephem-4-carboxylic acid (46.4 mg) as colorless powder.
Yield: 89.9%. mp. 117 - 122° C (decomposition).
UV: $\lambda_{max}^{CH_3OH}$ 276 nm ($\epsilon$=10200).
$[\alpha]_D^{25}$ − 15.3 ± 2.6° (c=0.216, CH$_3$OH).
IR: $\nu_{max}^{KBr}$ 1780, 1719, 1632 cm$^{-1}$.
NMR: $\delta^{D_2O}$ + $^{NaHCO_3}$ (3.45s + 3.53s)3H, (4.00s + 4.02s)3H, (4.08s + 4.13s)2H, (4.45s + 4.48s)2-3H, 5.12s1H, 6.87 + 7.28ABq(8Hz)4H.

Example III-16

To a solution of diphenylmethyl 7β-[α-p-hydroxyphenyl-α-(5-indanyl)oxycarbonylacetamido]-7α-methoxy-3-(1-methyltetrazol-5-yl)thiomethyl-1-oxadethia-3-cephem-4-carboxylate (150 mg) in methylene chloride (12 ml) are added anisole (0.4 ml) and trifluoroacetic acid (0.4 ml) at 0° C in nitrogen. After stirring for 20 minutes at 0° C, the reaction mixture is concentrated under reduced pressure, diluted with benzene, and concentrated. The residue is triturated with ether to give 7β-[α-p-hydroxyphenyl-α-(5-indanyl)oxycarbonylacetamido]-7α-methoxy-3-(1-methyltetrazol-5-yl)thiomethyl-1-oxadethia-3-cephem-4-carboxylic acid as powder (91 mg) melting at 123 - 126° C with decomposition.

Yield: 76.5%.

IR: $\nu_{max}^{KBr}$ 3385, 1785, 1727, 1705, 1631, 1613, 1595 cm$^{-1}$.

UV: $\lambda_{max}^{CH_3OH}$ 271.5 (ε=12950), 276.5 (ε=12700) nm. $[\alpha]_D^{22}$ + 1.3 ± 0.8°, $[\alpha]_{436}^{22}$ − 25.1 ± 1.2°, $[\alpha]_{546}^{22}$ − 5.2 ± 1.2° (c=0.541, CH$_3$OH).

EXAMPLE III-17

To a solution of diphenylmethyl 7β-[α-(p-benzyloxyphenyl)-α-benzyloxycarbonylacetamido]-7α-methoxy-3-(1-methyltetrazol-5-yl)thiomethyl-1-oxadethia-3-cephem-4-carboxylate (100 mg) in methylene chloride (2 ml) are added anisole (0.2 ml) and a solution of aluminum chloride (250 mg) in nitromethane (1.2 ml) under ice cooling. After stirring for 2 hours under ice cooling and for 1 hour at room temperature, the mixture is poured into a mixture of ethyl acetate and methanol (5:1), washed with 2N-hydrochloric acid and saturated saline, dried over sodium sulfate, and concentrated. The residue is washed with ether to give 7β-(α-p-hydroxyphenyl-α-carboxyacetamido)-7α-methoxy-3-(1-methyltetrazol-5-yl)thiomethyl-1-oxadethia-3-cephem-4-carboxylic acid (35 mg).

IR: $\nu_{max}^{KBr}$ 1780, 1719, 1632 cm$^{-1}$.

EXAMPLE III-18

To a solution of diphenylmethyl 7β-[α-t-butoxycarbonyl-α-(3-thienyl)acetamido]-7α-methoxy-3-(1-methyltetrazol-5-yl)-thiomethyl-1-oxadethia-3-cephem-4-carboxylate (144 mg) in anisole (0.3 ml) is added trifluoroacetic acid (1.7 ml) at 0° C in nitrogen gas. After stirring for 3 hours, the mixture is concentrated to dryness under reduced pressure, triturated with ether, and washed with ethyl acetate and ether to give 7β-[α-carboxy-α(3-thienyl)acetamido]-7α-methoxy-3-(1-methyltetrazol-5-yl)thiomethyl-1-oxadethia-3-cephem-4-carboxylic acid (61 mg) as light yellow powder. Yield: 61%. mp. 118 - 125° C (decomposition) from acetone. $[\alpha]_D^{25}$ - 12.8 ± 2.5° (c=0.211, CH$_3$OH).

UV: $\lambda_{max}^{CH_3OH}$ 276 nm (ε=10200).

IR: $\nu_{max}^{KBr}$ 1780, 1705 cm$^{-1}$.

NMR: $\delta^{D_2O\ +\ NaHCO_3}$ 4.03s3H, (4.11s + 4.21m)2H, (4.51s + 4.53s)2-3H, 5.15s1H, 7.05-7.25m1H, 7.27-7.52m2H.

EXAMPLE III-19

To a solution of diphenylmethyl 7β-[α-(3-thienyl)-α-diphenylmethoxycarbonylacetamido]-7α-methoxy-3-(1-methyltetrazol-5-yl)thiomethyl-1-oxadethia-3-cephem-4-carboxylate (830 mg) in methylane chloride (15 ml) are added anisole (2 ml) and trifluoroacetic acid (2 ml) under ice cooling. After stirring for 1 hour at the same temperature, the mixture is concentrated under reduced pressure. The residue is washed with ether to give 7β-[α-(3-thienyl)-α-carboxyacetamido]-7α-methoxy-3-(1-methyltetrazol-5-yl)thiomethyl-1-oxadethia-3-cephem-4-carboxylic acid as powder (383 mg) melting at 110–114° C, identified with an authertic specimen by comparison of IR spectra in KBr disc and thin layer chromatograms.

EXAMPLE III-20

To a solution of diphenylmethyl 7β-[α-(3-thienyl)-α-phenoxycarbonylacetamido]-7α-methoxy-3-(1-methyltetrazol-5-yl)-thiomethyl-1-oxadethia-3-cephem-4-carboxylate (100 mg) in methylene chloride (2 ml) are added anisole (0.2 ml) and trifluoroacetic acid (0.2 ml) under ice cooling. After stirring for 1 hour, the mixture is concentrated, and triturated in ether to give 7β-[α-(3-thienyl)-α-phenoxycarbonylacetamido]-7α-methoxy-3-(1-methyltetrazol-5-yl)thiomethyl-1-oxadethia-3-cephem-4-carboxylic acid as powder (38 mg) melting at 108–111° C. Yield: 50%.

IR: $\nu_{max}^{CHCl_3}$ 3400sh, 3325, 1788, 1745, 1705 cm$^{-1}$. $[\alpha]_D^{23}$ − 61.3 ± 2.0° (c=0.517, CHCl$_3$).

EXAMPLE III-21

To a solution of diphenylmethyl 7β-[α-(3-thienyl)-α-(3,4-dimethylphenyl)oxycarbonylacetamido]-7α-methoxy-3-(1-methyltetrazol-5-yl)thiomethyl-1-oxadethia-3-cephem-4-carboxylate (105 mg) in methylene chloride (2 ml) are added anisole (0.2 ml) and trifluoroacetic acid (0.2 ml) under ice cooling. After stirring for 1 hour, the mixture is concentrated under reduced pressure, triturated with ether, and filtrated. The solid is washed with ether and dried to give 7β-[α-(3-thienyl)-α-(3,4-dimethylphenyl)-oxycarbonylacetamido]-7α-methoxy-3-(1-methyltetrazol-5-yl)-thiomethyl-1-oxadethia-3-cephem-4-carboxylic acid as powder (64 mg) melting at 110–113° C. Yield: 77%.

IR: $\nu_{max}^{CHCl_3}$ 3400sh, 3325, 1787, 1737, 1704 cm$^{-1}$. $[\alpha]_D^{23}$ − 53.4 ± 1.9° (c=0.504, CHCl$_3$).

EXAMPLE III-22

To a solution of diphenylmethyl 7β-[α-(3-thienyl)-α-(indan-5-yl)oxycarbonylacetamido]-7α-methoxy-3-(1-methyltetrazol-5-yl)thiomethyl-1-oxadethia-3-cephem-4-carboxylate (97 mg) in methylene chloride (2 ml) are added anisole (0.3 ml) and trifluoroacetic acid (0.3 ml) under ice cooling. After stirring for 1 hour, the mixture is concentrated under reduced pressure and the residue is triturated with ether to give 7β-[α-(3-thienyl)-α-(5-indanyl)oxycarbonylacetamido]7α-methoxy-3-(1-methyltetrazol-5-yl)thiomethyl-1-oxadethia-3-cephem-4-carboxylic acid as powder (34 mg) melting at 111–113° C.

Yield: 45%.

IR: $\nu_{max}^{CHCl_3}$ 3406sh, 3335, 1789, 1744, 1704 cm$^{-1}$. $[\alpha]_D^{23}$ − 57.5 ± 2.4° (c=0.402, CHCl$_3$).

EXAMPLE III-23

To a solution of diphenylmethyl 7β-[α-diphenylmethoxycarbonyl-α-(2-thienyl)acetamido]-7α-methoxy-3-(1-methyltetrazol-5-yl)thiomethyl-1-oxadethia-3-cephem-4-carboxylate (140 mg) in methylene chloride are added anisole (0.2 ml) and trifluoroacetic acid (0.4 ml) at 0° C in nitrogen gas. After stirring for 1 hour at 0° C, the mixture is evaporated under reduced pressure, triturated with ether, and washed with ether to give 7β-[α-carboxy-α-(2-thienyl)acetamido]-7α-methoxy-3-(1- methyltetrazol-5-yl)-thiomethyl-1-oxadethia-3-cephem-4-carboxylic acid (60 mg) as colorless powder. Yield: 70%. mp. 104 - 109° C (decomposition).

UV: $\lambda_{max}^{CH_3OH}$ 275 nm ($\epsilon$=8800).
$[\alpha]_D^{24}$ − 15.0 ± 1.5° (c=0.374, CH$_3$OH).
IR: $\nu_{max}^{KBr}$ 1785, 1715 cm$^{-1}$.
NMR: $\delta^{D_2O\ +\ NaHCO_3}$ 7.00 − 7.5m3H, 5.15s1H, 4.04s3H, (3.54s + 3.48s)3H.

EXAMPLE III-24

To a solution of diphenylmethyl 7β-[α-(5-indanyl)oxycarbonyl-α-phenylacetamido]-7α-methoxy-3-(1-methyltetrazol-5-yl)-thiomethyl-1-oxadethia-3-cephem-4-carboxylate (116.1 mg) in methylene chloride are added anisole (0.1 ml) and trifluoroacetic acid (0.2 ml). After stirring for 30 minutes at 0° C, the mixture is evaporated under reduced pressure, chromatographed on silica gel (10 g) containing 10% water, eluted with ethyl acetate containing 5% acetic acid, and crystallized from a mixture of ether and pentane to give 7β-[α-(indan-5-yl)oxycarbonyl-α-phenylacetamido]-7α-methoxy-3-(1-methyltetrazol-5-yl)thiomethyl-1-oxadethia-3-cephem-4-carboxylic acid (74.5 mg) as colorless crystals.

Yield: 81.4%. mp. 123 - 125° C (decomposition).
IR: $\nu_{max}^{KBr}$ 1770, 1702 cm$^{-1}$.
$[\alpha]_D^{25}$ − 8.4 ± 1.4° (c=0.286, CH$_3$OH).
NMR: $\delta^{CDCl_3}$ 2.07s2H, 2.85s4H, (3.32s + 3.43s)3H, 3.79s3H, 4.25s2H, 4.50s2H, 4.69s1H, 4.97s1H.

EXAMPLE III-25

To a solution of diphenylmethyl 7β-(α-p-carbamoyloxyphenyl-α-diphenylmethoxycarbonylacetamido)-7α-methoxy-3-(1-methyltetrazol-5-yl)thiomethyl-1-oxadethia-3-cephem-4-carboxylate (170.1 mg) in methylene chloride (2 ml) are added anisole (0.4 ml) and trifluoroacetic acid (0.4 ml) at 0° C, and the mixture is stirred for 45 minutes, evaporated to dryness under reduced pressure, and triturated with ether to yield 7β-(α-p-carbamoyloxyphenyl-α-carboxyacetamido)-7α-methoxy-3-(1-methyltetrazol-5-yl)-thiomethyl-1-oxadethia-3-cephem-4-carboxylic acid (98.2 mg) as colorless powder. mp. 128 - 132° C.

IR: $\nu_{max}^{KBr}$ 1784, 1724(sh), 1710 cm$^{-1}$.
UV: $\lambda_{max}^{CH_3OH}$ 273 nm ($\epsilon$=9500).
$[\alpha]_D^{25}$ − 23.1 ± 0.7° (c=0.900, CH$_3$OH).

EXAMPLE III-26

In a procedure similar to that of Example III-25, diphenylmethyl 7β-(α-p-N-methylcarbomoyloxyphenyl-α-diphenylmethoxycarbonylacetamido)-7α-methoxy-3-(1-methyltetrazol-5-yl)-thiomethyl-1-oxadethia-3-cephem-4-carboxylate (100 mg) is treated with anisole (0.1 ml) and trifluoroacetic acid (0.1 ml) in methylene chloride (1 ml) at 0° C for 1 hour to give 7β-(α-p-N-methylcarbomoyloxyphenyl-α-carboxyacetamido)-7α-methoxy-3-(1-methyltetrazol-5-yl)-thiomethyl-1-oxadethia-3-cephem-4-carboxylic acid (52 mg) 49% yield. mp. 117 - 125° C.

IR: $\nu_{max}^{KBr}$ 3385, 1786, 1725 cm$^{-1}$.
UV: $\lambda_{max}^{CH_3OH}$ 271 nm ($\epsilon$=9532).

EXAMPLE III-27

In a procedure similar to that of Example III-25, diphenylmethyl 7β-(α-p-ureidocarbonyloxyphenyl-α-diphenylmethoxycarbonylacetamido)-7α-methoxy-3-(1-methyltetrazol-5-yl)thiomethyl-1-oxadethia-3-cephem-4-carboxylate (213 mg) is treated with anisole (0.4 ml) and trifluoroacetic acid (0.4 ml) in methylene chloride (3 ml) for 1 hour at 0° C to give 7β-(α-p-ureidocarbonyloxyphenyl-α-carboxyacetamido)-7α-methoxy-3-(1-methyltetrazol-5-yl)-thiomethyl-1-oxadethia-3-cephem-4-carboxylic acid (125 mg) 91% yield. mp. 137 - 142° C.

IR: $\nu_{max}^{KBr}$ 3440, 3330, 1780, 1712 cm$^{-1}$.
NMR: $\delta^{(CD_3)_2SO}$ (3.25s + 3.41s)3H, (3.90s + 3.93s)3H, 4.21brs2H, 4.98brs2H, 4.85brs1H, 5.05s1H, 7.20 − 7.15m2H, 7.13d(8Hz)2H, 7.42d(8Hz)2H, (9.15brs + 9.27brs)1H, 10.25brs1H.
UV- $\lambda_{max}^{CH_3OH}$ 276 nm ($\epsilon$=9105).

EXAMPLE III-28

To a solution of diphenylmethyl 7β-[α-p-(p-methoxybenzyl)oxyphenyl-α-diphenylmethoxycarbonylacetamido]-7α-methoxy-3-(1-methyltetrazol-5-yl)thiomethyl-1-oxadethia-3-cephem-4-carboxylate (170 mg) in methylene chloride (3.5 ml) are added anisole (0.35 ml) and trifluoroacetic acid (0.35 ml) at 0° C, and the mixture is stirred for 45 minutes at 0° C. After evaporation of the solvent, the product is triturated with ether to give 7β-(α-p-hydroxyphenyl-α-carboxyacetamido)-7α-methoxy-3-(1-methyltetrazol-5-yl)thiomethyl-1-oxadethia-3-cephem-4-carboxylic acid (91 mg) as colorless powder. Yield: nearly quantitative. mp. 125 - 132° C (decomposition).

EXAMPLE III-29

In a procedure similar to that of Example III-28, diphenylmethyl 7β-[α-p-(p-methoxybenzyl)oxyphenyl-α-p-methoxybenzyloxycarbonylacetamido]-7α-methoxy-3-(1-methyltetrazol-5-yl)-thiomethyl-1-oxadethia-3-cephem-4-carboxylate (1.45 g) is treated with anisole (4 ml) and trifluoroacetic acid (4 ml) in methylene chloride (8 ml) at 0° C for 40 minutes to give 7β-(α-p-hydroxyphenyl-α-carboxyacetamido)-7α-methoxy-3-(1-methyltetrazol-5-yl)-thiomethyl-1-oxadethia-3-cephem-4-carboxylic acid. mp. 125 - 132° C (decomposition). Yield: quantitative.

EXAMPLE III-30

(1) To a solution of diphenylmethyl 7β-[α-p-(p-methoxybenzyl)-oxy-phenyl-α-p-methoxybenzyloxycarbonyl-acetamido]-7α-methoxy-3-(1-methyltetrazol-5-yl)thiomethyl-1-oxadethia-3-cephem-4-carboxylate (1.20 g) in methylene chloride (24 ml) are added anisole (2.4 ml) and a solution of aluminum chloride (2.58 g) in nitromethane (12 ml) at 0° C under nitrogen. After stirring for 15 minutes at 0° C, the mixture is poured into cold 5% sodium hydrogencarbonate aqueous solution (100 ml) and filtered to remove the formed precipitate. The filtrate is washed twice with methylene chloride (2 × 100 ml), acidified with 2N-hydrochloric acid to pH 2.60, and poured in a column of high porous polymer HP-20 (60 ml) sold by Mitsubishi Chemical Industries Ltd. The column is washed with water (300 ml), and eluted with methanol. The eluate is concentrated under reduced pressure at room temperature. The residue is dissolved in methanol, treated with active carbon, and concentrated under reduced pressure to give 7β-(α-p-hydroxyphenyl-α-carboxyacetamido)-7α-methoxy-3-(1-methyl-tetrazol-5-yl)thiomethyl-1-oxadethia-3-cephem-4-carboxylic acid as powder (595 mg) decomposing at 125 - 132° C. Yield: 88.5%.

(2) The same product can be prepared in a method similar to that of above 1), wherein (a) p-methoxy-benzyl ether is substituted by benzyl ether
(b) p-methoxybenzyloxycarbonyl group is substituted by benzyloxycarbonyl group, and/or
(c) diphenylmethyl ester is substituted by benzyl ester.

IV. O-Acylation

Example IV-1

To a solution of diphenylmethyl 7β-(α-p-hydroxyphenyl-α-diphenylmethoxycarbonylacetamido)-7α-methoxy-3-(1-methyltetrazol-5-yl)thiomethyl-1-oxadethia-3-cephem-4-carboxylate (286 mg) in methylene chloride (2 ml) is added trichloroacetyl isocyanide (0.5 ml) while cooling at −78° C. After stirring at −78° C for 30 minutes and 0° C for 1 hour, the mixture is diluted with benzene (20 ml) and ethyl acetate (20 ml), washed with water, dried, and concentrated. The obtained residue is chromatographed on silica gel (30 g) containing 10% water and eluted with a mixture of benzene and ethyl acetate (1:1) to give diphenylmethyl 7β-(α-p-carbomoyloxyphenyl-α-diphenylmethoxycarbonylacetamido)-7α-methoxy-3-(1-methyltetrazol-5-yl)thiomethyl-1-oxadethia-3-cephem-4-carboxylate (179.9 mg) as colorless foam. Yield: 59.5%.

IR: $\nu_{max}^{CHCl_3}$ 3530, 3425, 3325, 1790, 1750, 1728, 1700sh cm$^{-1}$. NMR: $\delta^{CDCl_3}$ (3.42s + 3.45s)3H, 3.73s3H, 4.22s2H, 4.42s2H, 4.80s1H, 5.03s1H, 5.33s2H.

EXAMPLE IV-2

In a procedure similar to that described above in Example IV-1, diphenylmethyl 7β-(α-p-hydroxyphenyl-α-diphenylmethoxycarbonylacetamido)-7α-methoxy-3-(1-methyltetrazol-5-yl)thiomethyl-1-oxadethia-3-cephem-4-carboxylate (100 mg) is treated with methyl isocyanate (0.2 ml) in tetrahydrofuran (1 ml) in the presence of 1,5-diazabicyclo[3,5,0]undecene at 0° C for 4.5 hours to give diphenylmethyl 7β-(α-p-N-methylcarbomoyloxyphenyl-α-diphenylmethoxycarbonylacetamido)-7α-methoxy-3-(1-methyltetrazol-5-yl)thiomethyl-1-oxadethia-3-cephem-4-carboxylate (52 mg).

Yield: 49%.

IR: $\nu_{max}^{CHCl_3}$ 3460, 1785, 1725, 1700 cm$^{-1}$.

NMR: $\delta^{CDCl_3}$ 2.87d(5Hz)3H, 3.45brs3H, 3.80s3H, 4.23brs2H, 4.47brs2H, 4.77brs1H, 5.00s1H, 4.95 − 5.40m1H, 6.97s2H.

Example IV-3

In a procedure similar to that described above in Example IV-1, diphenylmethyl 7β-(α-p-carbomoyloxyphenyl-α-diphenylmethoxycarboxylacetamido)-7α-methoxy-3-(1-methyltetrazol-5-yl)thiomethyl-1-oxadethia-3-cephem-4-carboxylate (175 mg) is treated with trichloroacetyl isocyanide (0.4 ml) at 0° C in methylene chloride (2 ml) and at room temperature for 4 hours to give N³-trichloroacetylureidocarbonyloxyphenyl derivative, which is hydrolyzed with wet silica gel (10 g) for 1 hour in methylene chloride at room temperature to give diphenylmethyl 7α-(α-p-ureidocarbonyloxyphenyl-α-diphenylmethoxycarbonylacetamido)-7α-methoxy-3-(1-methyltetrazol-5-yl)thiomethyl-1-oxadethia-3-cephem4-carboxylate (145 mg). Colorless foam. Yield: 79%.

IR: $\nu_{max}^{CHCl_3}$ 3500, 1790, 1758, 1725, 1700sh cm$^{-1}$. NMR: $\delta^{CDCl_3}$ 3.43s3H, 3.68s3H, 4.21brs2H, 4.43brs2H, 4.83brs1H, 5.03s1H, 5.80 − 6.70m2H, 6.95s2H, 8.23brs1H, 9.20brs1H, 6.95s2H.

V. Protection

EXAMPLE V-1

To a suspension of 7β-(α-carboxy-α-phenylacetamido)-3-(1-methyltetrazol-5-yl)thiomethyl-1-oxadethia-3-cephem-4-carboxylic acid (400 mg) in methylene chloride (20 ml) is added diphenyldiazomethane (700 mg), and the mixture is stirred at room temperature for 30 minutes. The residue obtained by concentration under reduced pressure is chromatographed on silica gel (40 g) containing 10% water, and eluted with a mixture of benzene and ethyl acetate (1:1) to give diphenylmethyl 7β-(α-diphenylmethoxycarbonyl-α-phenylacetamido)-3-(1-methyltetrazol-5-yl)-thiomethyl-1-oxadethia-3-cephem-4-carboxylate (322 mg). mp. 107 − 109° C. Yield: 47.4%. (In another experiment, 95% yield of the product was obtained).

EXAMPLE V-2

To a suspension of 7β-(α-carboxy-α-phenylacetamido)-3-(1-methyltetrazol-5-yl)thiomethyl-1-oxadethia-3-cephem-4-carboxylic acid (50 mg) in a mixture of acetone (30 ml) and methanol (5 ml) is added a solution of sodium acetate (17.6 mg) in methanol (2 ml), and the mixture is stirred at room temperature for 1 hour. The reaction mixture is evaporated under reduced pressure, and the residue is washed with acetone to give disodium 7β-(α-carboxy-α-phenylacetamido)-3-(1-methyltetrazol-5-yl)thiomethyl-1-oxadethia-3-cephem-4-carboxylate (57 mg).

IR: $\nu_{max}^{KBr}$ 3425, 1746, 1660br, 1610br, 1410 cm$^{-1}$.

EXAMPLE V-3

The products of above Examples having free carboxy are dissolved in aqueous sodium hydrogencarbonate to give the corresponding sodium salts, of which the antibacterial activity is examined. These compounds are more active than the corresponding compounds having sulfur atom instead of oxygen atom at position 1 of the ring system. Those having 7α-methoxy are stronger antibiotics against gram negative bacteria resistant to common cephalosporins and also strongly active against *Pseudomonas aeruginosa* strains.

EXAMPLE V-4

To a solution of 7β-[α-(3-thienyl)-α-carboxyacetamido]-7α-methoxy-3-(1-methyltetrazol-5-yl)thiomethyl-1-oxadethia-3-cephem-4-carboxylic acid (2.04 g) in methanol (20 ml) is added a solution of sodium 2-ethylhexanoate in methanol (2mole/liter; 10 ml) at room temperature. After stirring for 10 minutes, the reaction mixture is diluted with ethyl acetate (100 ml), stirred for 5 minutes, and filtered to collect separated solid, which are washed with ethyl acetate, and dried to give disodium salt of 7β-[α-(3-thienyl)-α-carboxyacetamido]-7α-methoxy-3-(1-methyltetrazol-5-yl)thiomethyl-1-oxadethia-3-cephem-4-carboxylic acid (1.90 g). Yield: 86.7%. Colorless powder mp. decomposition from 150° C.

IR: $\nu_{max}^{KBr}$ 1768, 1680, 1612 cm$^{-1}$.
UV: $\lambda_{max}^{CH_3OH}$ 271 nm ($\epsilon$=9420).

EXAMPLE V-5

To a solution of 7β-(α-p-hydroxyphenyl-α-carboxyacetamido)-7α-methoxy-3-(1-methyltetrazol-5-yl)thiomethyl-1-oxadethia-3-cephem-4-carboxylic acid (359 mg) in methanol (7 ml) is added a solution of sodium 2-ethylhexanoate in methanol (2 mole/liter; 1.73 ml) at room temperature. After stirring for 10 minutes, the reaction mixture is diluted with ethyl acetate, stirred for 5 minutes, and filtered to collect separated solid, which is washed with ethyl acetate, and dried to give disodium salt of 7β-(α-p-hydroxyphenyl-α-carboxyacetamido)-7α-methoxy-3-(1-methyl-tetrazol-5-yl)thiomethyl-1-oxadethia-3-cephem-4-carboxylic acid (342 mg). Yield: 88.8%. Colorless powder. mp. decomposition from 170° C.

IR: $\nu_{max}^{Nujol}$ 1768, 1675, 1608 cm$^{-1}$.
UV: $\lambda_{max}^{CH_3OH}$ 273 nm ($\epsilon$=11100).

EXAMPLE V-6

To a solution of 7β-[α-p-hydroxyphenyl-α-carboxyacetamido]-7α-methoxy-3-(1-methyltetrazol-5-yl)thiomethyl-1-oxadethia-3-cephem-4-carboxylic acid (836 mg) in a mixture of methylene chloride (15 ml), ethyl acetate (15 ml) and methanol (10 ml) is added diphenyldiazomethane (950 mg). After stirring for 30 minutes at room temperature, the mixture is concentrated under reduced pressure, and washed with n-hexane. The product is chromatographed on silica gel (90 g) containing 10% water, and eluted with a mixture of benzene and ethyl acetate (1:1) to give diphenylmethyl 7β-(α-p-hydroxyphenylα-diphenylmethoxycarbonylacetamido)-7α-methoxy-3-(1 -methyltetrazol-5-yl)thiomethyl-1-oxadethia-3-cephem-4-carboxylate (1.270 g). Yield: 95%.

IR: $\nu_{max}^{CHCl_3}$ 3585, 3315, 1790, 1722, 1700sh cm$^{-1}$.

VI. COMPOSITION AND THEIR USE

EXAMPLE VI-1

Disodium salt of 7β-(α-p-hydroxyphenyl-α-carboxyacetamido)-7α-methoxy-3-(1-methyltetrazol-5-yl)thiomethyl-1-oxadethia3-cephem-4-carboxylic acid (100 mg) in a 5 ml vial is dissolved in sterilized water for injection (1 ml) before use, and given to an adult patient suffering from pyelitis by way of intravenus injection.

EXAMPLE VI-2

Lyophilizate from a solution of 7β[α-(3-thienyl)-α-carboxyacetamido]-7α-methoxy-3-(1-methyltetrazol-5-yl)thiomethyl1-oxadethia-3-cephem-4-carboxylic acid (1 g) neutralized to pH 7.0 with sodium hydrogen carbonate is placed in a 150 ml vial. The lyophilizate is dissolved in sterilized water for injection (100 ml) and dripped intravenously to an adult patient immediately after or during a surgical operation of cancer for preventing and treating post operative bacterial infection.

EXAMPLE VI-3

Mycrocrystalline 7β-[α-carbamoyloxyphenyl-α-carboxyacetamido]-7α-methoxy-3-(1-methyltetrazol-5-yl)thiomethyl-1-oxadethia3-cephem-4-carboxylic acid (200 mg) in a 5 ml vial is suspended in sterilized water for injection containing 2 mg of procaine (2 ml), and given intramuscularly to a patient suffering from suppurative inflammation caused by Staphylococcus aureus.

EXAMPLE VI-4

Crystalline 7β-[α-(3-thienyl)-α-(5-indanyl)oxycarbonylacetamido]-3-(1-methyltetrazol-5-yl)thiomethyl-1-oxadethia-3-cephem-4-carboxylic acid (200 mg) is dissolved in sesame oil (0.25 ml) and filled in a hard gelatin capsule. Each one capsule is given orally at 4 hour intervals to a patient suffering from upper respiratory tract infection caused by Streptococcus pyogenes.

EXAMPLE VI-5

Powdered 7β-(α-p-hydroxyphenyl-α-(5-indanyl)oxycarbonylacetamido]-7α-methoxy-3-(1-methyltetrazol-5-yl)thiomethyl-1-oxodethia-3-cephem-4-carboxylic acid (100 mg) is mixed well with corn starch (150 mg) and talc (10 mg), powdered, and encapsulated in a hard gelatin capsule (250 mg volume). Each one capsule is administered orally at 3 hour intervals to an adult patient suffering from urinary tract infection caused by Escherichia coli.

EXAMPLE VI-6

Mixed powder of 7β-[α-p-carbamoyloxyphenyl-α-(5-indanyloxy)carbonylacetamido]-7α-methoxy-3-(1-methyltetrazol-5-yl)thiomethyl-1-oxadethia-3-cephem-4-carboxylic acid (10 g), lactose (50 g), corn starch (2 g), magnesium stearate (0.3 g), sucrose (10 g), and necessary amount of acacia and talc is granulated. The granule is mixed with water before use to obtain a suspension, and one teaspoonful amount of the suspension is given orally to an infant suffering from pneumonia caused by Klebsiella pneumoniae.

What we claim is:

1. A compound selected from the group consisting of (a) a compound of the formula

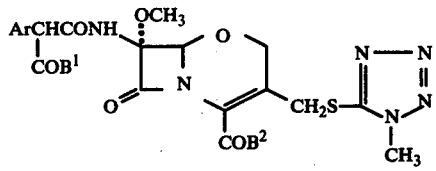

wherein
Ar is

in which Acyl is alkanoyl containing 1 to 5 carbon atoms, carbamoyl, N-alkylcarbamoyl containing 2 to 6 carbon atoms, or ureidocarbonyl;

COB$^1$ and COB$^2$ each is carboxy, methoxycarbonyl, ethoxycarbonyl, isopropoxycarbonyl, n-butoxycarbonyl, t-butoxycarbonyl, pentyloxycarbonyl, cyclopropylmethoxycarbonyl, monohydroxy-t-butoxycarbonyl, 2,2,2-trichloroethoxycarbonyl, chloromethoxycarbonyl, cyanomethoxycarbonyl, methanesulfonylethoxycarbonyl, acetylmethoxycarbonyl, acetoxymethoxycarbonyl, acetoxyethoxycarbonyl, propionyloxymethoxycarbonyl, propionyloxyethoxycarbonyl, pivaloyloxymethoxycarbonyl, benzoyloxymethoxycarbonyl, methoxymethoxycarbonyl, phenoxymethoxycarbonyl, methylthiomethoxycarbonyl, phenylthiomethoxycarbonyl, α,α-dimethylpropargyloxycarbonyl, methoxycarbonyloxyethoxycarbonyl, ethoxycarbonylethoxycarbonyl, methoxycarbonyloxypropoxycarbonyl, allyloxycarbonyl, benzyloxycarbonyl, phenethyloxycarbonyl, tolylmethoxycarbonyl, dimethylbenzyloxycarbonyl, nitrobenzyloxycarbonyl, halobenzyloxycarbonyl, methoxybenzyloxycarbonyl, p-hydroxy-di-t-butylbenzyloxycarbonyl, diphenylmethoxycarbonyl, trityloxycarbonyl, phenacyloxycarbonyl, chlorophenacyloxycarbonyl, bromophenacyloxycarbonyl, nitrophenacyloxycarbonyl, methylphenacyloxycarbonyl, trimethylsilyloxycarbonyl, dimethylmethoxysilyloxycarbonyl, trimethylstannyloxycarbonyl, phenoxycarbonyl, naphthyloxycarbonyl, tolyloxycarbonyl, dimethylphenoxycarbonyl, nitrophenoxycarbonyl, methoxyphenoxycarbonyl, methanesulfonylphenoxycarbonyl, chlorophenoxycarbonyl, pentachlorophenoxycarbonyl, indanyloxycarbonyl, sodiooxycarbonyl, potassiooxycarbonyl, magnesiooxycarbonyl, calciooxycarbonyl, or a salt of carboxy group with procain, xylocain, triethylamine, or dicyclohexylamine;

and (b) when at least one of $COB^1$ and $COB^2$ is carboxy, a pharmaceutically acceptable salt thereof.

2. A compound selected from the group consisting of (a) a compound according to claim 1, wherein each of $COB^1$ and $COB^2$ is carboxy, acetoxymethoxycarbonyl, pivaloyloxymethoxycarbonyl, acetoxyethoxycarbonyl, propionyloxyethoxycarbonyl, indanyloxycarbonyl, phenoxycarbonyl, tolyloxycarbonyl, dimethylphenoxycarbonyl, methoxyphenoxycarbonyl, methoxycarbonyloxyethoxycarbonyl, ethoxycarbonyloxymethoxycarbonyl, or phenacyloxycarbonyl, and (b) when at least one $COB^1$ or $COB^2$ is carboxy, a pharmaceutically acceptable salt thereof.

3. A compound selected from the group consisting of 7β-(α-phenyl-α-carboxyacetamido)-7α-methoxy-3-(1-methyltetrazol-5-yl)thiomethyl-1-oxadethia-3-cephem-4-carboxylic acid and a sodium or potassium salt thereof.

4. A compound according to claim 1 wherein Ar is p-hydroxyphenyl.

5. A compound selected from the group consisting of (a) a compound according to claim 1 wherein $COB^1$ is carboxy, acetoxymethoxycarbonyl, pivaloyloxymethoxycarbonyl, acetoxyethoxycarbonyl, propionyloxyethoxycarbonyl, indanyloxycarbonyl, phenoxycarbonyl, tolyloxycarbonyl, dimethylphenoxycarbonyl, methoxyphenoxycarbonyl, methoxycarbonyloxyethoxycarbonyl, ethoxycarbonyloxymethoxycarbonyl or phenacyloxycarbonyl, and (b) when $COB^1$ is carboxy, a pharmaceutically acceptable salt of the compound.

6. A compound selected from the group consisting of (a) a compound according to claim 5 wherein $COB^2$ is carboxy and (b) a pharmaceutically acceptable salt thereof.

7. A compound according to claim 1 that is 7β-(α-p-hydroxyphenyl-α-carboxyacetamido)-7α-methoxy-3-(1-methyl-tetrazol-5-yl)thiomethyl-1-oxadethia-3-cephem-4-carboxylic acid.

8. A compound according to claim 1 that is sodium salt of 7β-(α-p-hydroxyphenyl-α-carboxyacetamido)-7α-methoxy-3-(1-methyltetrazol-5-yl)thiomethyl-1-oxadethia-3-cephem-4-carboxylic acid.

9. A compound according to claim 1 that is potassium salt of 7β-(α-p-hydroxyphenyl-α-carboxyacetamido)-7α-methoxy-3-(1-methyltetrazol-5-yl)thiomethyl-1-oxadethia-3-cephem-4-carboxylic acid.

10. A compound according to claim 1 that is 7β-[α-p-hydroxyphenyl-α-(5-indanyloxy)carbonylacetamido]-7α-methoxy-3-(1-methyltetrazol-5-yl)thiomethyl-1-oxadethia-3-cephem-4-carboxylic acid.

11. A compound according to claim 1 that is sodium salt of 7β-[α-p-hydroxyphenyl-α-(5-indanyloxy)carbonylacetamido]-7α-methoxy-3-(1-methyltetrazol-5-yl)thiomethyl-1-oxadethia-3-cephem-4-carboxylic acid.

12. A compound according to claim 1 wherein Ar is p-acyloxyphenyl.

13. A compound according to claim 12 wherein Ar is carbamoyloxyphenyl.

14. A compound according to claim 13 that is 7β-(α-p-carbamoyloxyphenyl-α-carboxyacetamido)-7α-methoxy-3-(1-methyl-tetrazol-5-yl)thiomethyl-1-oxadethia-3-cephem-4-carboxylic acid.

15. A compound according to claim 13 that is sodium salt of 7β-(α-p-carbamoyloxyphenyl-α-carboxylacetamido)-7α-methoxy-3-(1-methyltetrazol-5-yl)thiomethyl-1-oxadethia-3-cephem-4-carboxylic acid.

16. A compound according to claim 13 that is potassium salt of 7β-(α-p-carbamoyloxyphenyl-α-carboxyacetamido)-7α-methoxy-3-(1-methyltetrazol-5-yl)thiomethyl-1-oxadethia-3-cephem-4-carboxylic acid.

17. A compound selected from the group consisting of the compound 7β-(α-p-acetoxyphenyl-α-carboxyacetamido)-7α-methoxy-3-(1-methyl-tetrazol-5-yl)thiomethyl-1-oxadethia-3-cephem-4-carboxylic acid and a sodium or potassium salt thereof.

18. A compound selected from the group consisting of the compound 7β-(α-p-N-methylcarbamoyloxyphenyl-α-carboxyacetamido-7α-methoxy-3-(1-methyltetrazol-5-yl)thiomethyl-1-oxadethia-3-cephem-4-carboxylic acid and a sodium or potassium salt thereof.

19. A compound selected from the group consisting of the compound 7β-(α-p-ureidocarbonyloxyphenyl-α-carboxyacetamido)-7α-methoxy-3-(1-methyltetrazol-5-yl)thiomethyl-1-oxadethia-3-cephem-4-carboxylic acid and a sodium or potassium salt thereof.

20. A bactericidal composition comprising a bactericidally effective amount of a compound according to claim 1 and a pharmaceutically acceptable carrier.

21. A composition according to claim 20 containing 0.01% to 99% of the active compound.

22. A composition according to claim 21 in dosage unit form.

23. A composition according to claim 22 suitable for injection.

24. A composition according to claim 23 in a form suitable for injection in an ampule or vial.

25. A composition according to claim 23 in the form of powder, crystals, microcrystals or lypholizate in a vial.

26. A composition according to claim 23 wherein Ar is p-hydroxyphenyl, or p-carbamoyloxyphenyl and $COB^1$ and $COB^2$ each is carboxy in the form of the sodium or potassium salt.

27. A composition according to claim 23 wherein the compound is the sodium or potassium salt of 7β-(α-p-hydroxyphenyl-α-carboxyacetamido)-7α-methoxy-3-(1-methyltetrazol-5-yl)thiomethyl-1-oxadethia-3-cephem-4-carboxylic acid.

28. A composition according to claim 23 wherein the compound is the sodium or potassium salt of 7β-(α-p-carbamoyloxyphenyl-α-carboxyacetamido)-7α-methoxy-3-(1-methyltetrazol-5-yl)thiomethyl-1-oxadethia-3-cephem-4-carboxylic acid.

29. A composition according to claim 22 suitable for enteral administration.

30. A composition according to claim 29 in the form of capsule, tablet or dry syrup.

31. A composition according to claim 29 wherein Ar is p-hydroxyphenyl or carbamoyloxyphenyl; $COB^1$ is indanyl, phenyl, or dimethylphenyl; $COB^2$ is carboxy or a sodium or potassium salt thereof.

32. A method for treating human or veterinary bacterial infection comprising the administration to a patient a bactericidally effective amount of a compound according to claim 1.

33. A method according to claim 32 for treating human or veterinary bacterial infection selected from the group consisting of pneumonia, bronchitis, pneumonitis, empyema, nasopharyngitis, tonsillitis, rhinitis, dermatitis, pustulosis, ulceration, absess, wound and soft tissue infection, ear infections, osteomyelitis, septicemia, gastroenteritis, enteritis, urinary tract infections, and pyelonephritis, when caused by bacteria sensitive to the active compound or for preventing post operative infection.

34. A method according to claim 32 wherein the compound is administered at a daily dose of 0.05 to 50 mg per kilogram body weight when the compound is given by injection.

35. A method according to claim 32 wherein the compound is administered at a daily dose of 0.5 to 200 mg per kilogram of body weight when the compound is administered orally.

36. A method according to claim 32 wherein the compound is administered at a daily dose of 1 μg to 1 mg when the compound is given topically.

37. A method according to claim 32 wherein Ar is p-hydroxyphenyl, or p-carbamoyloxyphenyl and $COB^1$ and $COB^2$ each is carboxy in the form of the free acid or a pharmaceutically acceptable salt thereof.

38. A method according to claim 32 wherein the compound is the sodium or potassium salt of 7β-(α-p-hydroxyphenyl-α-carboxyacetamido)-7α-methoxy-3-(1-methyltetrazol-5-yl)thiomethyl-1-oxadethia-3-cephem-4-carboxylic acid.

39. A method according to claim 32 wherein the compound is the sodium or potassium salt of 7β-(α-p-carbamoyloxyphenyl-α-carboxyacetamido)-7α-methoxy-3-(1-methyltetrazol-5-yl)thiomethyl-1-oxadethia-3-cephem-4-carboxylic acid.

40. A method according to claim 32 wherein Ar is p-hydroxyphenyl, or p-carbamoyloxyphenyl; $COB^1$ is phenoxycarbonyl, dimethylphenoxycarbonyl, or indanyloxycarbonyl; $COB^2$ is carboxy; in the form of the free acid or a pharmaceutically acceptable salt thereof.

41. A method according to claim 40 wherein the compound is 7β-[α-p-hydroxyphenyl-α-(5-indanyloxy)-carbonylacetamido]-7α-methoxy-3-(1-methyltetrazol-5-yl)thiomethyl-1-oxadethia-3-cephem-4-carboxylic acid or a sodium salt thereof.

* * * * *

UNITED STATES PATENT AND TRADEMARK OFFICE
CERTIFICATE OF CORRECTION

PATENT NO. : 4,138,486               Page 1 of 4
DATED     : February 6, 1979
INVENTOR(S) : MASAYUKI NARISADA and WATARU NAGATA It is certified that error appears in the above-identified patent and that said Letters Patent are hereby corrected as shown below:

Page 1 of the patent, the right hand column, the formulas appearing at line 4 (counting the formulas as one line each), the right hand formula, correct the formula to read:

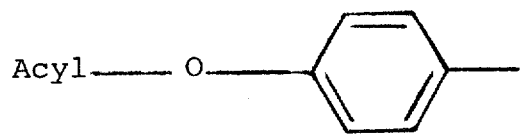

Column 1, to the left of the formulas appearing between lines 31 and 35, delete "Het is";

line 65, change "1-oxade-" to --1-oxadethiace- --.

Column 2, line 12, change "negative b bacteria;" to --negative bacteria'--.

Column 7, line 31, correct the spelling of "grouping".

UNITED STATES PATENT AND TRADEMARK OFFICE
CERTIFICATE OF CORRECTION

PATENT NO. : 4,138,486
DATED : February 6, 1979
INVENTOR(S) : MASAYUKI NARISADA and WATARU NAGATA It is certified that error appears in the above-identified patent and that said Letters Patent are hereby corrected as shown below:

Column 10, correct the formula appearing at line 45 to read:

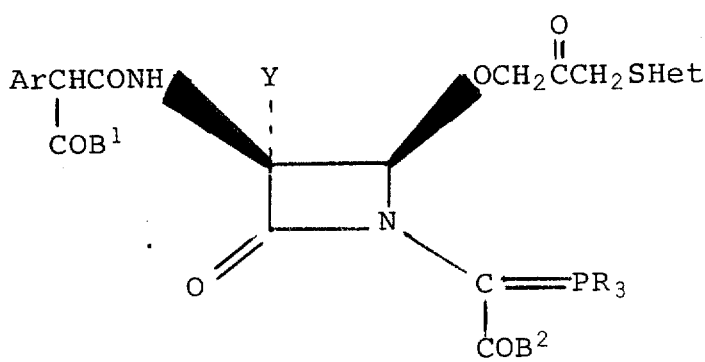

Column 13, line 36, change "7α-amino" to --7β-amino--.

Column 17, line 39, after "acetic" change "and" (first occurrence) to --acid--.

Column 24, line 24, change "tone" to --tene--.

Column 28, line 12, change "7β-(60-" to read --7β-(α- --.

UNITED STATES PATENT AND TRADEMARK OFFICE
CERTIFICATE OF CORRECTION

PATENT NO. : 4,138,486           Page 3 of 4
DATED : February 6, 1979
INVENTOR(S) : MASAYUKI NARISADA and WATARU NAGATA It is certified that error appears in the above-identified patent and that said Letters Patent are hereby corrected as shown below:

Column 39, line 50, change "N-methylcarbomoyloxyphe-" to

--N-methylcarbamoyloxyphe- --;

line 56, change "N-methylcarbomoyloxyphenyl" to

--N-methylcarbamoyloxyphenyl--.

Column 41, line 22, change "carbomoyloxyphenyl" to

--carbamoyloxyphenyl--;

line 51, change "carbomoylox-" to --carbamoylox- --.

UNITED STATES PATENT AND TRADEMARK OFFICE
CERTIFICATE OF CORRECTION

PATENT NO. : 4,138,486

DATED : February 6, 1979

INVENTOR(S) : MASAYUKI NARISADA and WATARU NAGATA

It is certified that error appears in the above-identified patent and that said Letters Patent are hereby corrected as shown below:

Column 43, line 25, change "hydroxyphenylα" to read --hydroxyphenyl-α --;

line 53, correct the spelling of "Microcrystalline".

Signed and Sealed this

Twenty-seventh Day of January 1981

[SEAL]

Attest:

RENE D. TEGTMEYER

Attesting Officer

Acting Commissioner of Patents and Trademarks